United States Patent [19]
Kuhrts et al.

[11] Patent Number: 5,981,555
[45] Date of Patent: Nov. 9, 1999

[54] COMPOSITIONS, KITS AND METHODS FOR ADMINISTRATION OF ANTILIPEMIC DRUGS

[75] Inventors: Eric H. Kuhrts, Woodside, Calif.; L. Jackson Roberts, II; Jason D. Morrow, both of Nashville, Tenn.

[73] Assignees: Lipoprotein Technologies, Inc., Woodside, Calif.; Vanderbilt University, Nashville, Tenn.

[21] Appl. No.: 08/937,669

[22] Filed: Sep. 26, 1997

Related U.S. Application Data

[63] Continuation-in-part of application No. 08/425,057, Apr. 19, 1995, Pat. No. 5,773,453, and a continuation-in-part of application No. 08/425,060, Apr. 19, 1995, abandoned, and a continuation-in-part of application No. 08/548,822, Oct. 26, 1995, abandoned.

[51] Int. Cl.⁶ .......................... A61K 31/715; A61K 31/33
[52] U.S. Cl. .......................... 514/356; 514/404; 514/405; 514/420; 514/568; 514/569; 514/570; 514/823
[58] Field of Search ...................................... 514/356, 568, 514/569, 570, 420, 404, 405, 823

[56] References Cited

U.S. PATENT DOCUMENTS

| | | | |
|---|---|---|---|
| 4,965,252 | 10/1990 | Kuhrts | 514/54 |
| 5,023,245 | 6/1991 | Kuhrts | 514/54 |
| 5,041,430 | 8/1991 | Addicks et al. | 514/161 |
| 5,292,534 | 3/1994 | Valentine et al. | 424/451 |
| 5,401,730 | 3/1995 | Sauvage et al. | 514/165 |

OTHER PUBLICATIONS

Medline Abstract #85225813, Hamazaki et al, Apr. 1985.
Medline Abstract #82137645, Wilkin et al, Apr. 1982.
Medline Abstract #77263172, Anderson et al, Jul. 1977.
Andersson, et al., Acta pharmacol. et toxicol. 41:1–10 (1997).
Ding et al, Am. Coll. Clin Pharm., Abstract.
Ding et al, 2nd Cardio. Pharm. Int'l. Symp., Abstract 6.
Ding et al, "Dose–Dependent Nicotinic Acid Induced Flush", Abstract 7a.
Ding et al, "Does Aspirin Block the Nicotinic Acid Induced Flush?", Abstract 7.
Ding et al, Clin. Pharmacol. Ther., 46(6):642–647 (1989).
Hamazaki et al, Elsevier Scientific Publishers Ireland, Ltd. (1985).
Helgason et al, Stroke, 25:2331–2336 (1994).
Kaijser et al, Medical Biology, 57:114–117, 1979.
King et al, Americal J. of Medicine, 97:323–331, Oct. 1994.
Kreisberg et al, American J. of Medicine, 97:313–316, Oct. 1994.
Lasagna. JAMA, 271(9):709–710, 1994.
McKenney et al, JAMA, 271(9) 672–677, 1994.
Morrowet al, J. of Investig. Dermatology, 98:812–815, 1992.
Morrow et al, Prostaglandins, 38(2):263–274, 1989.
Stern et al, Clin Pharmacol Ther, 50(1):66–70, 1991.
Svedmyr et al, Acta pharmacol. et toxicol, 41:397–400, 1977.
Whelan et al, J. Fam. Prac., 34(2):165–168, 1992.
Wilkin et al, Clin. Pharmacol. Ther., 31(4):478–482, 1982.
Wilkin et al, Clin. Pharmacol. Ther., 38(3):273–277, 1985.

*Primary Examiner*—Keith D. MacMillan
*Attorney, Agent, or Firm*—Birch, Stewart, Kolasch & Birch, LLP

[57] ABSTRACT

The present invention concerns composition, kits and methods for reducing the flushing effect (cutaneous erythema) of an antilipemic drug, for treating hyperlipemia, for improving the effectiveness of an anti-platelet aggregating drug (e.g., in nonresponders) and for treating thrombosis. The present compositions and kits for reducing the flushing effect and for treating hyperlipemia contain an antilipemic drug (such as niacin) and either a sustained release NSAID (such as aspirin) or an NSAID and a carboxylic acid compound other than the NSAID and antilipemic drug. The kits contain (a) pre-dosages of the NSAID and optional carboxylic acid compound and (b) an antilipemic dosage of the antilipemic drug, which optionally may be combined with NSAID and optional carboxylic acid compound in an amount effective to maintain the reduction of the flushing effect. The present method of treating hyperlipemia comprises predosing the patient with a sustained release NSAID or an NSAID and a carboxylic acid compound other than the NSAID and antilipemic drug at least 2 hours before administering the antilipemic drug. The present compositions and kits for increasing the effectiveness of an anti-platelet aggregating drug contain an NSAID such as aspirin, niacin or a congener thereof, and optionally, a carboxylic acid other than the NSAID, such as citric acid.

28 Claims, 6 Drawing Sheets

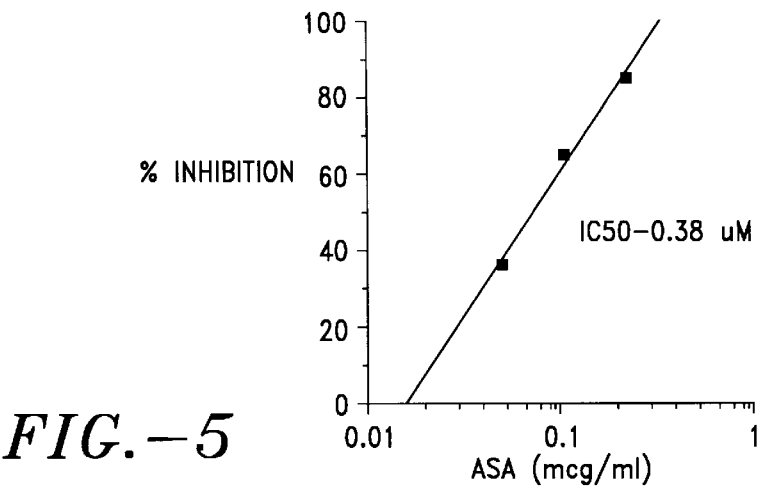
FIG.-5 DOSE-RESPONSE CURVE FOR INHIBITION OF PG RELEASE IN HUMAN MONCYTIC THP-1 CELLS BY ASPIRIN
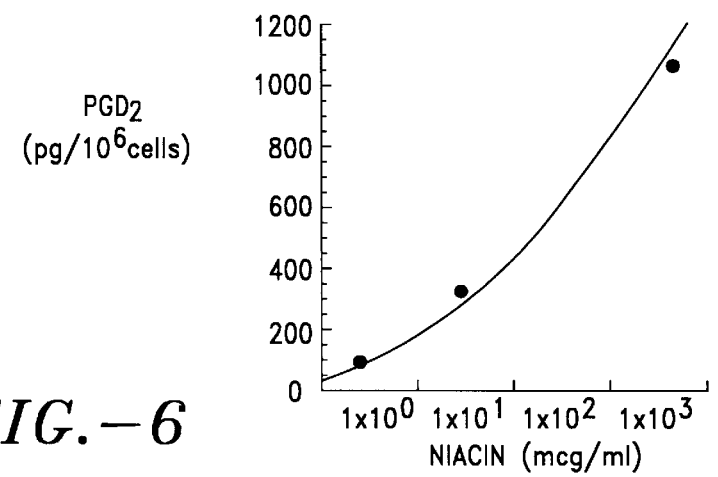
FIG.-6 NIACIN-INDUCED RELEASE OF $PGD_2$ FROM KUPFFER CELL MACROPHAGES
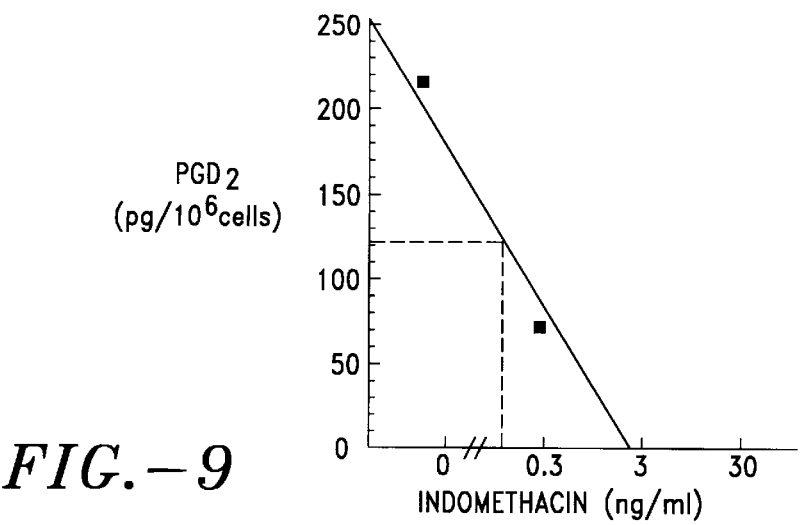
FIG.-9

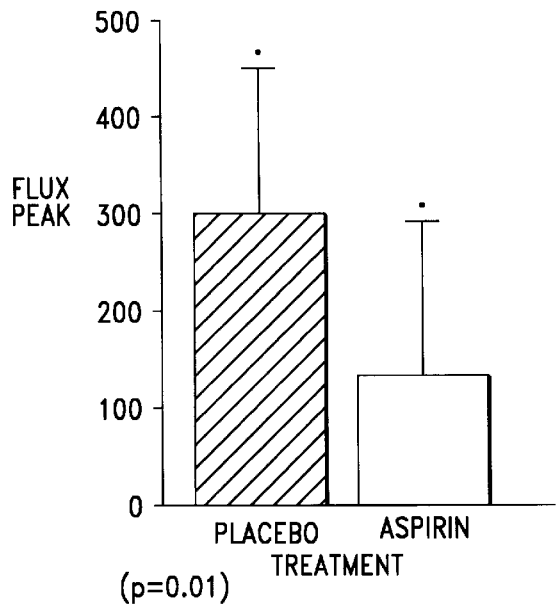
FIG.—10A
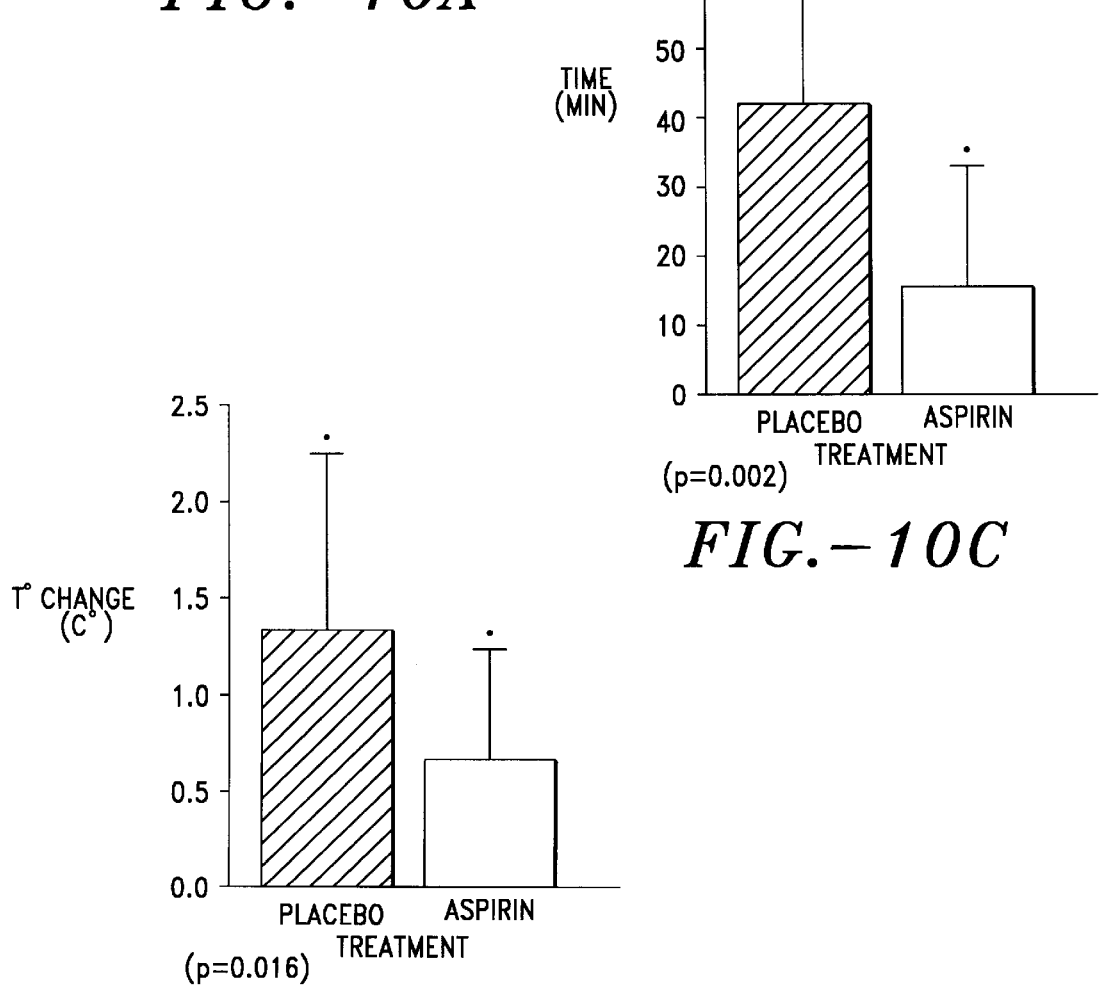
FIG.—10C
FIG.—10B

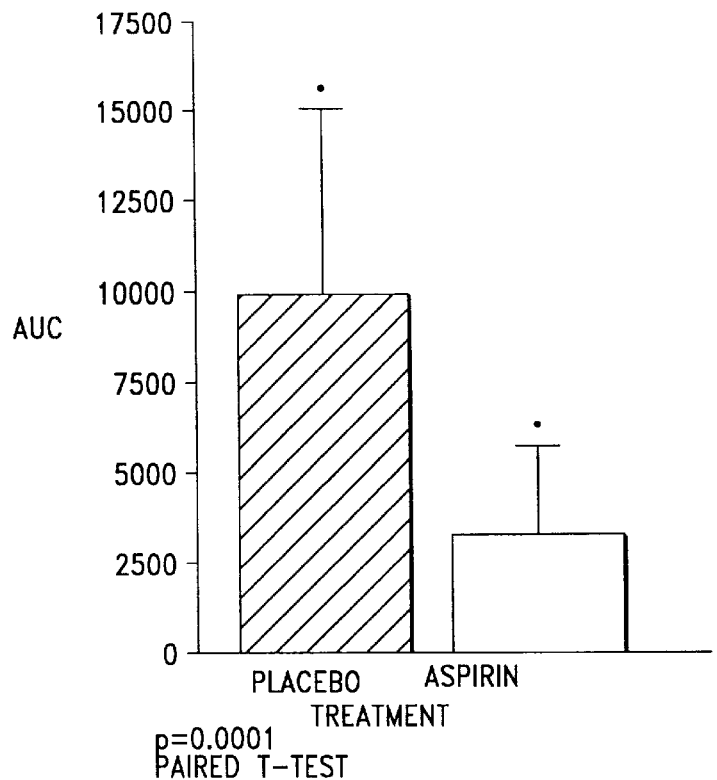
FIG.—11A
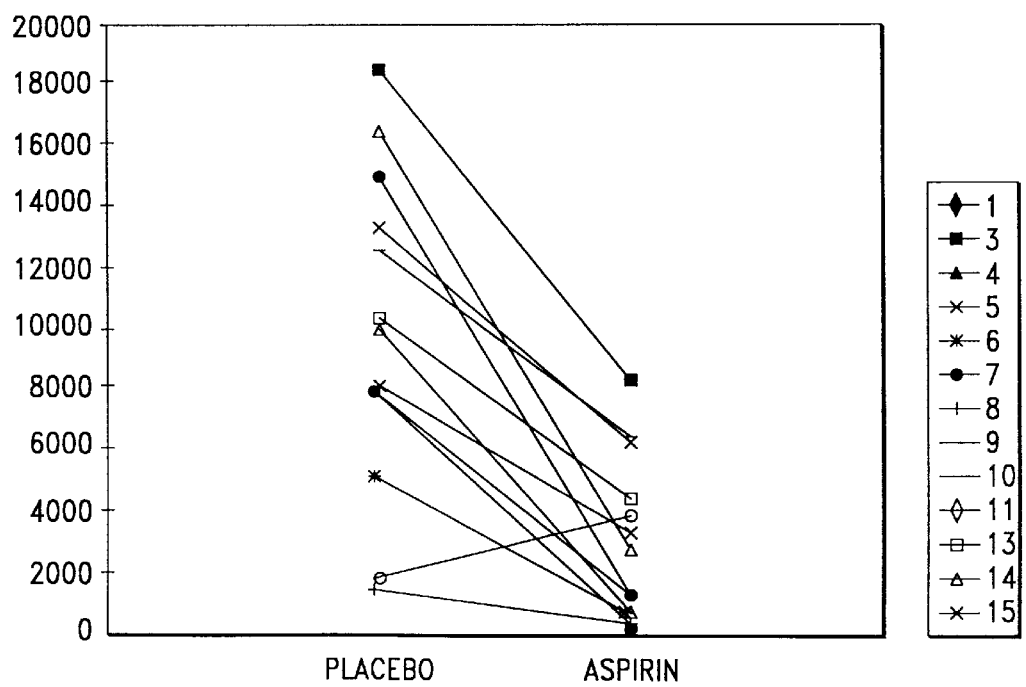
FIG.—11B

006E

COMPOSITIONS, KITS AND METHODS FOR ADMINISTRATION OF ANTILIPEMIC DRUGS

RELATED APPLICATIONS

This application is a continuation-in-part of pending U.S. application Ser. No. 08/425,057, filed Apr. 19, 1995, U.S. Pat. No. 5,773,453 Ser. No. 08/425,060, filed Apr. 19, 1995 abandoned, and Ser. No. 08/548,822, filed Oct. 26, 1995 abandoned, the disclosures of which are hereby incorporated by reference herein in their entirety.

FIELD OF THE INVENTION

The present invention concerns compositions, kits and methods for administration of antihyperlipidemic (i.e., hypolipemic or antilipemic) drugs, particularly nicotinic acid and its derivatives, which decrease the flushing reaction caused by such drugs. The present invention also concerns compositions, kits and methods for increasing the effectiveness of nonsteroidal anti-inflammatory drugs in inhibiting or preventing platelet aggregation in non-responding patients.

BACKGROUND

Abnormally high levels of circulating lipids (hyperlipidemias) are a major predisposing factor in development of atherosclerosis. Elevated levels of serum cholesterol and cholesteryl esters, which are carried by the beta-lipoprotein or low density lipoprotein (LDL) and lipoprotein (a) (Lp(a)) fractions of serum lipids, are known to be atherogenic. Also implicated in cardiovascular disease are elevated levels of triglycerides, carried mostly in the very low density lipoprotein (VLDL) fraction.

Drugs which lower serum lipids (i.e., hypolipemic drugs) frequently are prescribed to retard development of atherosclerotic lesions in individuals exhibiting hyperlipidemias. Many of these drugs are effective when taken regularly, but suffer from poor patient compliance due to unpleasant side effects. Examples of effective but underutilized hypolipemic drugs include the bile acid-binding resins, such as cholestyramine.

The ability of large doses of nicotinic acid (i.e., niacin) to lower serum lipid levels has been recognized for many years. This drug is unusually effective because it lowers the levels of several classes of morbidity-associated serum lipids, including LDL cholesterol (LDL-C), Lp(a), and triglycerides (Tg). In addition to its antilipemic activity, niacin is also an essential water-soluble vitamin. Nicotinic acid exhibits relatively low toxicity on a molar basis.

However, the doses required to lower atherogenic serum lipids are quite large, on the order of 1–8 grams per day. At these levels, adverse side effects are frequent, and may include gastrointestinal disturbances such as nausea, heartburn, and diarrhea. However, the most frequent and prominent side effect is intense flushing, often accompanied by cutaneous itching, tingling, or warmth, and occasionally by headache. Although the flushing side effect is in general harmless, it is sufficiently unpleasant that patient compliance is markedly reduced. Often, 30–40% of patients cease taking nicotinic acid within days after initiating therapy. Consequently, significant efforts have been exerted to develop niacin analogs, dosage forms, and treatment protocols which minimize the flush reaction.

Tolerance to the flush reaction develops after a few days or weeks of repeated administration of nicotinic acid. One strategy for administration is to begin with low doses, i.e., 125 mg twice daily, then to increase the daily dose by increments of 30–100% after 1–6 weeks at each dose level; see, e.g., McKenney et al., *J. Am. Med. Assn.* 271:672–710 (1994). This procedure reduces but does not eliminate the flush reaction. Ibid. A further difficulty with relying upon tolerance for suppression of the flush reaction is that tolerance is lost rapidly if the drug is discontinued for a day or two. Consequently, the dose must be reduced again when administration is resumed.

Another method of reducing flush is to administer a sustained release (SR) form of nicotinic acid. Sustained release preparations reportedly have a lower incidence of flushing and gastrointestinal side effects, and concomitantly greater patient compliance and tolerance; see King et al., *Am. J. Med.* 97:323–331, 329 (1994); Knopp et al., *Metabolism* 34:642–650 (1985); Alderman et al., *Am. J. Cardiol.* 64:725–729 (1989).

However, even sustained release preparations are not tolerated by a significant fraction of the patient population; see Luria et al., *Arch. Into Med.* 148:2493–2495 (1988). Moreover, sustained release dosage forms are prone to induce a much more severe side effect, hepatic toxicity; see, e.g., Rader et al., *Am. J. Med.* 92:77–81 (1992).

Recent studies have indicated that the flushing reaction is initiated by release of prostaglandin D. Prostaglandins are known to cause vasodilation, as well as a subjective experience of discomfort. Evidence supporting the role of prostaglandin D in mediating the niacin-induced flush includes the observation that a dramatic rise in the concentration of prostaglandin F2, a metabolite of D, occurs in the blood coming from the skin following administration of niacin. Furthermore, the level of prostaglandin F2 decreases markedly after 6 days of continuous, twice daily administration of nicotinic acid. This decrease in nicotinic acid-induced prostaglandin F2 correlates with the development of tolerance to the flush reaction which usually develops upon prolonged administration. Therefore, tolerance appears to reflect a decline in prostaglandin D release, rather than an increase in metabolic inactivation of nicotinic acid.

Several nonsteroidal anti-inflammatory drugs (NSAIDs) have been shown to inhibit the synthesis of one or more prostaglandins (PGs) by blocking the enzyme prostaglandin synthetase, also referred to as cyclooxygenase. Among the NSAIDs in clinical use are aspirin, ibuprofen, naproxen, phenylbutazone, indomethacin, and flufenamic acid and its congeners. These NSAIDs inhibit the synthesis of PGs such as E2 and F2, but typically at high micromolar ($\mu$M) concentrations; see, e.g., Flower, *Pharmacol. Rev.* 26:33 (1974) (see Table 1 therein).

The prostaglandin synthetase inhibitors aspirin and indomethacin have been shown to reduce the cutaneous flush induced by nicotinic acid. Anderson et al., *Acta Pharmacol. Toxicol.* 41:1–10 (1977), demonstrated that nicotinic acid-induced flush in guinea pigs, as measured by an increase in ear temperature, was inhibited by pretreatment at 4.5 and 0.5 hr with indomethacin (25 or 50 mg/kg) or aspirin (50,100, or 200 mg/kg). An aspirin total dose of 975 mg, administered to human subjects in a divided dose of 650 mg at 1 hr and 325 mg at 0.5 hr prior to high dose nicotinic acid challenge, was shown to significantly reduce cutaneous flush; see Wilken et al. *Clin. Pharmacol. Ther.* 31:478–482 (1982).

A nicotinic acid ester derivative, methyl nicotinate, which causes local cutaneous erythema when administered topically, was used to study the flush-inhibiting effects of aspirin.

The effect of aspirin on niacin-induced cutaneous reactions has been studied clinically; see Whelan et al. *J. Fam. Pract.* 34:165–168 (1992). The authors of this study concluded that 325 mg of aspirin will decrease the warmth and flushing associated with niacin, but not the itching and tingling. In this study, either aspirin or a placebo was administered 30 minutes prior to niacin. As compared to the control group (to whom a placebo was administered prior to niacin), an 80 mg dose of aspirin appeared to have caused even more aggravated flushing, warmth, itching and tingling than pre-administration of the placebo. However, even a 325 mg dose of aspirin administered 30 minutes prior to niacin resulted in flushing and warmth in at least 72% of the patients.

NSAIDs such as aspirin inhibit cyclooxygenase and are therefore considered prostaglandin synthetase inhibitors. Thus, aspirin is considered to be the best NSAID for prevention of platelet aggregation (thrombosis) because it is a long-lasting inhibitor of platelet cyclooxygenase, and it irreversibly acetylates the enzyme. Platelet cyclooxygenase cannot by restored by protein biosynthesis because platelets lack a nucleus.

With regard to inhibiting platelet aggregation, the ex vivo effect of aspirin has been studied in patients taking aspirin for recurrent ischemic stroke prevention; see Helgason et al. *Stroke* 25:2331–2336 (1994). In this study, increasing doses of aspirin were administered to patients with previous ischemic stroke, and the extent of platelet aggregation inhibition was determined periodically. Over 33 months of initial testing, 288 out of 306 patients had complete inhibition, and 78 out of 306 had partial inhibition. However, at repeat testing, about 33% of the patients having complete inhibition at initial testing had lost part of the anti-platelet effect of aspirin and had converted from complete to partial inhibition without a change in aspirin dosage. Of 52 patients with partial inhibition at initial testing, 35 achieved complete inhibition either by dosage escalation or fluctuation of response at the same dosage, but 8 of the 35 reverted to partial inhibition on further testing. Thus, the anti-platelet (and presumably antithrombotic) effect of a fixed dose of aspirin was not constant over time in all individuals. Furthermore, the mechanisms by which the increased dosage requirement of aspirin resistance develop, and the clinical significance of this development, remained undefined.

Further, a method for reducing platelet aggregation in which patients having a predisposition for thrombus formation are treated with compositions of aspirin, citric acid, thiamine and/or a zinc salt is known (see U.S. Pat. No. 5,401,730; incorporated herein by reference in its entirety). The combination of aspirin and citric acid is believed to be more effective than aspirin alone. Further, thiamine is believed to contribute to the reduction in thrombotic potential by reducing plasma fibrinogen levels.

SUMMARY OF THE INVENTION

It is an object of the present invention to provide compositions, kits and methods for administration of antilipemic drugs which reduce the health risks associated with long-term use of moderate dosages of NSAIDs.

It is a further object of the present invention to provide compositions, kits and methods for administering antilipemic drugs which are easy to use and which minimize risks associated with reliance on patient compliance.

It is a further object of the present invention to provide compositions, kits and methods which increase the effectiveness of NSAIDs in reducing the flushing effect caused by antilipemic drugs such as nicotinic acid, including the flushing and warmth caused in those patients who do not respond well to administration of NSAIDs alone.

These and other objects of the present invention, which will become readily apparent from the following detailed description of the preferred embodiments, have been achieved, in part, by compositions and kits comprising niacin and/or a congener thereof, an NSAID such as aspirin (which may be in a sustained release formulation) to improve the reduction in flushing produced by niacin, and optionally, a carboxylic acid compound other than niacin (nicotinic acid) or the NSAID; and, in part, by methods for administering antilipemic drugs and for increasing the effectiveness of NSAIDs in the inhibition or prevention of platelet aggregation using the present compositions and kits.

The present invention provides a pharmaceutical composition for administering hypolipemic amounts of niacin having reduced capacity to provoke a flushing reaction in a subject. The composition comprises (1) a hypolipemic amount of niacin, and (2) a nonsteroidal anti-inflammatory drug (NSAID). The NSAID is selected from the group consisting of aspirin, ibuprofen, indomethacin, phenylbutazone, and naproxen, and the NSAID is present in an amount effective to reduce cutaneous flushing caused by the niacin. The NSAID is present in an amount up to the following amount for that member: aspirin, 160 mg; ibuprofen, 160 mg; indomethacin, 10 mg; phenylbutazone, 100 mg; naproxen, 100 mg. The amount of niacin is preferably 50 mg–2 g, more preferably, 500 mg–2 g. The NSAID may be in immediate release or sustained release dosage form.

Also disclosed herein is a method of suppressing cutaneous erythema in a patient to whom niacin is administered. The method comprises administering to the patient an amount of (a) a nonsteroidal anti-inflammatory drug (NSAID), and (b) a carboxylic acid compound other than the NSAID or niacin effective to reduce the cutaneous erythema prior to niacin being administered to, released in or absorbed by the patient. The NSAID is selected from the group consisting of aspirin, ibuprofen, indomethacin, phenylbutazone, and naproxen. The NSAID is administered in an amount within the following range for that member: aspirin, 10–160 mg; ibuprofen, 5–160 mg; indomethacin, 2–10 mg; phenylbutazone, 1–100 mg; naproxen, 5–100 mg.

The NSAID and carboxylic acid compound are preferably administered at least 2 hours; more preferably, from 2 hours to 7 days; most preferably, from 2 to 24 hours, prior to niacin being administered to, released in or absorbed by the patient. The NSAID is preferably aspirin and is administered in an amount of from 10 to 40 mg from 2 to 4 times daily. The NSAID is preferably in a sustained release formulation, and is preferably aspirin in a sustained release formulation providing an amount of from 3 mg to 100 mg of aspirin per hour to the patient. The carboxylic acid compound is preferably citric acid.

Also disclosed herein is a method of treating hyperlipemia comprising administering to a patient in need thereof niacin as an antilipemic drug, a nonsteroidal anti-inflammatory drug (NSAID) and a carboxylic acid compound other than the NSAID or niacin. The NSAID and the carboxylic acid compound are administered in an amount effective to reduce cutaneous erythema which niacin causes in the patient, and the niacin is administered in an amount effective to treat the hyperlipemia. The NSAID is selected from the group consisting of aspirin, ibuprofen, indomethacin, phenylbutazone, and naproxen. The NSAID is administered in an amount within the following range for that member: aspirin, 10–160 mg; ibuprofen, 5–160 mg; indomethacin, 2–10 mg; phenylbutazone, 1–100 mg; naproxen, 5–100 mg.

The niacin is preferably administered in a manner resulting in niacin being released in or absorbed by the patient at least 2 hours after the NSAID and the carboxylic acid compound are administered. The NSAID is preferably aspirin administered in an amount of from 10 to 40 mg from 2 to 4 times daily. The NSAID is preferably in a sustained release formulation, and is preferably aspirin in a sustained release formulation providing an amount of from 3 mg to 100 mg of aspirin per hour to the patient. The carboxylic acid compound is preferably citric acid, administered in an amount of from 50 to 500 mg.

Also disclosed herein is a composition for treating hyperlipemia, comprising: an effective amount of niacin to treat the hyperlipemia, a nonsteroidal anti-inflammatory drug (NSAID), and a carboxylic acid compound other than the NSAID or niacin. The NSAID and the carboxylic acid compound are present in a combined amount effective to reduce cutaneous erythema caused by the effective amount of niacin. The NSAID is selected from the group consisting of aspirin, ibuprofen, indomethacin, phenylbutazone, and naproxen. The NSAID is present in an amount up to the following amount for that member: aspirin, 160 mg; ibuprofen, 160 mg; indomethacin, 10 mg; phenylbutazone, 100 mg; naproxen, 100 mg.

The carboxylic acid compound is preferably citric acid. The NSAID is preferably aspirin, and the composition provides a sustained release of the aspirin in an amount of from 3 mg to 100 mg per hour to the patient. The niacin is preferably enterically coated. The composition preferably comprises a bilayer tablet having first and second layers, in which the first layer comprises the enterically coated niacin, and the second layer comprises the NSAID and the carboxylic acid compound.

Also disclosed herein is a kit for treating hyperlipemia, comprising at least one unit dosage comprising an effective amount of niacin to treat hyperlipemia, and at least one unit pre-dosage of a nonsteroidal anti-inflammatory drug (NSAID) and a carboxylic acid compound other than the NSAID or niacin effective to prevent or inhibit cutaneous erythema caused by niacin in a patient. The NSAID is selected from the group consisting of aspirin, ibuprofen, indomethacin, phenylbutazone, and naproxen. The unit pre-dosage provides an amount of NSAID within the following range for that member: aspirin, 10–160 mg; ibuprofen, 5–160 mg; indomethacin, 2–10 mg; phenylbutazone, 1–100 mg; naproxen, 5–100 mg.

The unit dosage preferably further comprises an amount of the NSAID and the carboxylic acid compound effective to maintain suppression of the cutaneous erythema. The unit pre-dosage is preferably a sustained release formulation, which is preferably a sustained release formulation of aspirin providing an amount of from 3 mg to 100 mg of aspirin per hour to the patient. The carboxylic acid compound is preferably citric acid.

The unit dosage is preferably enterically coated. The unit pre-dosage and the unit dosage preferably comprise a bilayer tablet having first and second layers, wherein the first layer comprises an enterically coated formulation containing the unit dosage, and the second layer comprises the unit pre-dosage. The first layer is preferably an inner layer, and the second layer is preferably an outer layer.

Also disclosed herein is a composition for treating hyperlipemia, comprising: (a) an amount of an enterically coated niacin effective to treat the hyperlipemia, and (b) an amount of a nonsteroidal anti-inflammatory drug (NSAID) effective to reduce cutaneous erythema caused by niacin. The NSAID is selected from the group consisting of aspirin, ibuprofen, indomethacin, phenylbutazone, and naproxen. The NSAID is present in an amount up to the following amount for that member: aspirin, 160 mg; ibuprofen, 160 mg; indomethacin, 10 mg; phenylbutazone, 100 mg; naproxen, 100 mg.

Also disclosed herein is a method of suppressing cutaneous erythema in a patient to whom niacin is administered, comprising administering to the patient an amount of a sustained release nonsteroidal anti-inflammatory drug (NSAID) effective to reduce the cutaneous erythema caused by niacin. The NSAID is administered in an amount providing from 3 mg to 100 mg of NSAID per hour to the patient from 4 to 12 hours prior to niacin being administered to, released in, or absorbed by the patient.

Also disclosed herein is a method of suppressing cutaneous erythema in a patient to whom niacin is administered, comprising administering to the patient an amount of a sustained release aspirin effective to reduce the cutaneous erythema caused by niacin. The aspirin is administered in an amount providing from 3 mg to 100 mg of aspirin per hour to the patient at least 2 hours prior to niacin being administered to, released in, or absorbed by the patient.

Also disclosed herein is a method of treating hyperlipemia, comprising (a) administering to a patient in need of niacin as an antilipemic drug an amount of a sustained release aspirin effective to reduce cutaneous erythema which niacin causes in the patient and in an amount of from 3 mg to 100 mg of aspirin per hour to the patient, and (b) administering to the patient an effective amount of niacin to treat the hyperlipemia. The niacin is administered in a manner resulting in niacin being released in or absorbed by the patient at least two hours after the aspirin is administered.

Also disclosed herein is a kit for treating hyperlipemia, comprising: (a) at least one unit dosage comprising an effective amount of niacin to treat hyperlipemia, and (b) at least one unit pre-dosage of a sustained release aspirin effective to treat or inhibit cutaneous erythema caused by niacin in a patient. The unit pre-dosage provides an amount of the sustained release aspirin of from 3 mg to 100 mg per hour in the patient.

The present invention also provides a pharmaceutical composition for administration of hypolipemic amounts of niacin having reduced capacity to provoke a flushing reaction in a subject, comprising (1) a hypolipemic amount of niacin, and (2) a nonsteroidal anti-inflammatory drug (NSAID). The NSAID is present in an amount effective to reduce cutaneous flushing caused by the niacin. The NSAID is present in an amount that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone. The amount of niacin is preferably 50 mg–2 g, more preferably, 500 mg–2 g. The NSAID may be in immediate release or sustained release dosage form.

Also disclosed herein is a method of suppressing cutaneous erythema in a patient to whom niacin is administered, comprising administering to the patient an amount of (a) a nonsteroidal anti-inflammatory drug (NSAID), and (b) a carboxylic acid compound other than the NSAID or niacin effective to reduce the cutaneous erythema prior to niacin being administered to, released in or absorbed by the patient. The NSAID is administered in an amount that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone. The NSAID and the carboxylic acid compound are preferably administered at least 2 hours; more preferably, 2 hours to 7 days; most preferably, 2 to 24 hours, prior to niacin being administered to, released in or absorbed by the patient. The NSAID is preferably in a sustained release formulation. The carboxylic acid compound is preferably citric acid.

Also disclosed herein is a method of treating hyperlipimia, comprising administering to a patient in need thereof niacin as an antilipemic drug, a nonsteroidal anti-inflammatory drug (NSAID) and a carboxylic acid compound other than the NSAID or niacin. The NSAID and the carboxylic acid compound are administered in an amount effective to reduce cutaneous erythema which niacin causes in the patient, and the niacin is administered in an amount effective to treat the hyperlipemia. The NSAID is administered in an amount that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

The niacin is preferably administered in a manner resulting in niacin being released in or absorbed by the patient at least 2 hours after the NSAID and the carboxylic acid compound are administered. The NSAID is preferably in a sustained release formulation. The carboxylic acid compound is preferably citric acid, administered in an amount of from 50 to 500 mg.

Also disclosed herein is a composition for treating hyperlipemia, comprising: an effective amount of niacin to treat the hyperlipemia, a nonsteroidal anti-inflammatory drug (NSAID), and a carboxylic acid compound other than the NSAID or niacin. The NSAID and the carboxylic acid compound are present in a combined amount effective to reduce cutaneous erythema caused by the effective amount of niacin. The NSAID is present in an amount that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone. The carboxylic acid compound is preferably citric acid. The niacin is preferably enterically coated. The composition preferably comprises a bilayer tablet having first and second layers, in which the first layer comprises the enterically coated niacin, and the second layer comprises the NSAID and the carboxylic acid compound.

Also disclosed herein is a kit for treating hyperlipemia, comprising at least one unit dosage comprising an effective amount of niacin to treat hyperlipemia, and at least one unit pre-dosage of a nonsteroidal anti-inflammatory drug (NSAID) and a carboxylic acid compound other than the NSAID or niacin effective to prevent or inhibit cutaneous erythema caused by niacin in a patient. The unit pre-dosage provides an amount of NSAID that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone. The unit dosage preferably further comprises an amount of the NSAID and the carboxylic acid compound effective to maintain suppression of the cutaneous erythema. The unit pre-dosage is preferably a sustained release formulation. The carboxylic acid compound is preferably citric acid.

The unit dosage is preferably enterically coated. The unit pre-dosage and the unit dosage preferably comprise a bilayer tablet having first and second layers, wherein the first layer comprises an enterically coated formulation containing the unit dosage, and the second layer comprises the unit pre-dosage. The first layer is preferably an inner layer, and the second layer is preferably an outer layer.

Also disclosed herein is a composition for treating hyperlipemia, comprising: (a) an amount of an enterically coated niacin effective to treat the hyperlipemia, and (b) an amount of a nonsteroidal anti-inflammatory drug (NSAID) effective to reduce cutaneous erythema caused by niacin. The NSAID is present in an amount that is less than the minimum anti-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

Also disclosed herein is a method of suppressing cutaneous erythema in a patient to whom niacin is administered, comprising administering to the patient an amount of a sustained release nonsteroidal anti-inflammatory drug (NSAID) effective to reduce the cutaneous erythema caused by niacin. The NSAID is administered in an amount providing an amount of NSAID per hour that is less than the minimum hourly non-inflammatory dose for that NSAID from 4 to 12 hours prior to niacin being administered to, released in, or absorbed by the patient. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

Also disclosed herein is a method of suppressing cutaneous erythema in a patient to whom niacin is administered, comprising administering to the patient an amount of a sustained release aspirin effective to reduce the cutaneous erythema caused by niacin. The NSAID is administered in an amount providing an amount of NSAID per hour that is less than the minimum hourly non-inflammatory dose for that NSAID at least 2 hours prior to niacin being administered to, released in, or absorbed by the patient. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

Also disclosed herein is a method of treating hyperlipemia, comprising (a) administering to a patient in need of niacin as an antilipemic drug an amount of a sustained release aspirin effective to reduce cutaneous erythema which niacin causes in the patient and in an amount providing an amount of NSAID per hour that is less than the minimum hourly non-inflammatory dose for that NSAID, and (b) administering to the patient an effective amount of niacin to treat the hyperlipemia. The niacin is administered in a manner resulting in niacin being released in or absorbed by the patient at least two hours after the NSAID is administered. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

Also disclosed herein is a kit for treating hyperlipemia, comprising: (a) at least one unit dosage comprising an effective amount of niacin to treat hyperlipemia, and (b) at least one unit pre-dosage of a sustained release NSAID effective to treat or inhibit cutaneous erythema caused by niacin in a patient. The unit pre-dosage provides an amount per hour of the sustained release NSAID that is less than the minimum hourly non-inflammatory dose for that NSAID. The NSAID is preferably selected from the group consisting of aspirin, ibuprofen, indomethacin, naproxen, piroxicam, ketoprofen, fenoprofen, oxaprozin, sulindac, flurbiprofen, etodolac, diclofenac, ketorolac, tolmetin, and nabumetone.

BRIEF DESCRIPTION OF THE DRAWINGS

FIG. 5 is a graph showing a dose-response curve for inhibition of PG release from THP-1 cells by aspirin.

FIG. 6 is a graph showing release of PGD2 from Kupfer cells induced by various niacin concentrations.

FIG. 9 is a graph showing inhibition of prostaglandin production in the human macrophage THP-1 cell line in vitro by indomethacin concentrations.

FIGS. 10A, 10B and 10C are graphs showing the flux change (A), local $T^o$ change (B) and flushing duration (C) in accordance with a clinical study comparing an embodiment of the present invention with a placebo.

FIGS. 11A and 11B show the mean area under the curve (AUC) (A) and a graph of the scatter plot of individual AUCs (B) in the controlled study described in Example 7 hereinbelow.

DETAILED DESCRIPTION OF THE INVENTION

Figure 1:
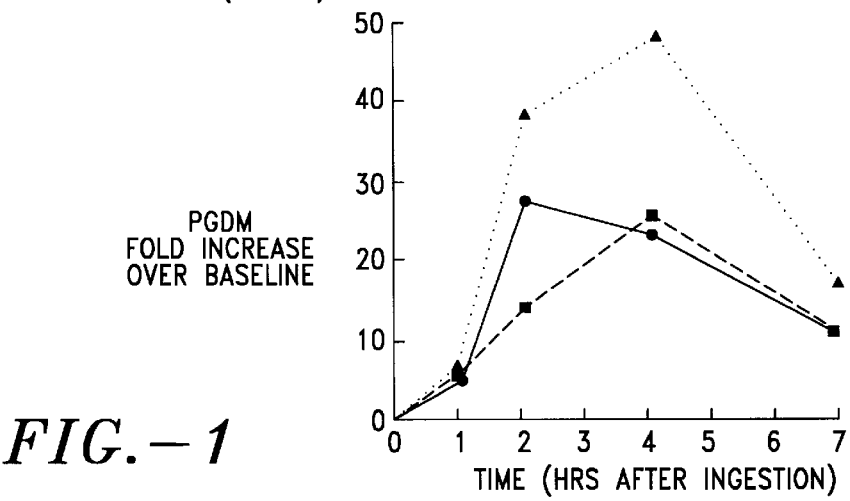
FIG. 1 is a graph showing the increase in excretion of PGD-M, the major urinary metabolite of PDG2, in human subjects over 7 hours following ingestion of 500 mg nicotinic acid; triangles indicate subject 1, circles indicate subject 2, and squares indicate subject 3.

The method of this invention for reducing the nicotinate-induced cutaneous erythema flushing reaction in a patient comprises administering to the patient a flush-inhibiting regimen of a non-steroidal anti-inflammatory drug (NSAID) in amounts which are effective to reduce the cutaneous erythema. The amounts administered are substantially less than are required to produce an effective anti-inflammatory response since anti-inflammatory levels reduce the proportion of patients who respond favorably to the treatment, that is, for some patients, anti-inflammatory levels are not effective to prevent flushing while the amounts of NSAIDs prescribed in this invention are effective. The amounts administered are preferably equal to or less than 75% of the dose required to produce an effective anti-inflammatory response.

The mechanism of the NSAID's action is believed to be its acetylation and deactivation of the prostaglandin F2-producing cyclooxygenase, thereby reducing the amount of active enzyme and its PG F2 product to a level which does not produce significant flushing. The regimen of administering the NSAID is limited only by its effectiveness to provide and maintain the requisite level of NSAID to cause this result, and the NSAID can be administered in traditional or non-traditional tablet, capsule, liquid, skin patch, intravenous solution, subcutaneous implant, sustained release, delayed release and immediate release, or other dosage forms in amounts and in regimens which produce this result. To be most effective, the enzyme level should be reduced before administration of the nicotinate, and the NSAID is therefore preferably administered a sufficient time before the nicotinate is administered to prevent initiation of flushing.

The dosage regimen suitable for this method can include prolonged multi-day dosing of small doses of NSAID with a regimen which accumulates NSAID to produce an effective amount before the nicotinate level reaches a flush-inducing level, or it can be a regimen which produces the effective level within a shorter time. Nicotinates can be administered in immediate release, delayed release or sustained release forms, or mixtures of any of these forms. Sustained release forms of nicotinate have been suggested because they produce a lower incidence of flushing.

The phrase "flush-reducing regimen of non-steroidal anti-inflammatory drug" is defined herein to mean a regimen of non-steroidal anti-inflammatory drug doses in any dosage form or composition which is effective to reduce nicotinate-induced cutaneous erythema at the beginning, during or after nicotinate administration, and which is substantially less than is required to produce an effective anti-inflammatory response.

The phrase "flush-reducing amount and dosage form of non-steroidal anti-inflammatory drug" is defined to mean an amount which, in its dosage form, will reduce nicotinate-induced cutaneous erythema when administered with a nicotinate, the amount being substantially less than is required to produce an effective anti-inflammatory response in that dosage form. It will be apparent that the total amount of NSAID in a slow or sustained release formulation which satisfies this definition may, if formulated in an immediate release NSAID formulation, be sufficient to produce an anti-inflammatory response.

The term "NSAID" is defined to mean "non-steroidal anti-inflammatory drug".

The term "nicotinate" is defined to mean nicotinic acid and its congeners such as methyl nicotinate.

The term "NSAID-resistant subjects" is defined to mean subjects in which some flush-producing PG F2 levels continue after treatment with NSAID, and does not include those subjects who are resistant to the effects of NSAIDs altogether.

The present invention provides methods for administration of antihyperlipidemic amounts of nicotinic acid and its anti-hyperlipidemic congeners (herein collectively referred to as nicotinates) so that the flush reaction is lessened or prevented. The methods involve pretreatment of a subject with a nonsteroidal anti-inflammatory drug agent (NSAID) in an amount sufficient to inhibit synthesis of prostaglandin D2 (PGD2) by monocyte-derived skin cells, especially macrophage-like cells such as Langerhans cells. The pretreatment is continued for a period of 1–6 days prior to administration of the nicotinate, preferably for at least 2 days, more preferably at least 3 days, and typically within the range of 2–4 days. Pretreatment beyond 3–4 days generally does not provide additional enhancement of the protection against flushing, but does preserve the protective effect and may be practiced within the scope of the invention.

During pretreatment, the NSAID is administered in at least one dose daily, preferably two or more doses daily. In most cases, four or fewer doses are preferred for the convenience and concomitantly improved compliance of the patient or subject. The dosage form may provide immediate release (IR) or sustained release (SR) of the NSAID. An sustained release dosage form may be administered fewer times daily than a comparable immediate release form, while providing similar protective serum concentrations of the NSAID.

The methods further provide for continued administration of the NSAID while the nicotinate is being administered. The nicotinate may be administered initially at a dosage level which is sufficient to produce hypolipemic effects in the subject, or may be administered initially at a lower level and raised progressively to hypolipemic dosage levels. This latter procedure allows induction of nicotinate tolerance to occur simultaneously with inhibition of flush by an NSAID.

A preferred nicotinate is nicotinic acid itself, which optionally may be provided as a salt. Other hypolipemic nicotinates include esters of nicotinic acid, such as lower alcohol esters (e.g., methyl, ethyl, or propyl esters).

When the nicotinate is an immediate release form of nicotinic acid itself, a hypolipemic dose level typically is at least 500 mg per day, often at least 500–750 mg or 750 mg–1 g, 1–0.5 g, or even up to 1.5–2 g daily. Sustained release forms of nicotinate may be administered in lower dosages, often one-half the immediate release dosage. The daily dosage of nicotinate frequently is divided into multiple doses taken, e.g., 2–4 times daily. For purposes of defining the invention, a "hypolipemic amount" of nicotinate includes an amount which initially may be less than the amount which produces clinically significant hypolipemia, e.g., less than 500 mg for an immediate release form, provided that the daily dose is increased over time to a clinically effective hypolipemic amount. This allows for development of tolerance in conjunction with the use of NSAIDs to lessen flush. An initial dosage of a subtherapeutic but tolerance-inducing amount of nicotinate typically will be capable of provoking at least some flushing reaction, e.g., 50–200 mg. This dosage may be increased gradually until dosages of 500 mg or greater are achieved.

Particularly preferred NSAIDs include aspirin, ibuprofen, naproxen, phenylbutazone, indomethacin, piroxicam, ketoprofen, fenoprofen, oxaprozin, sulindac, flurbiprofen, etodolac, diclofenac, ketorolac, tolmetin, and nabumetone. These are administered in dosages that are less than the usual dosage ranges for treatment of pain and inflammation. In preferred embodiments, the NSAID is administered in dosage ranges equal to or less than 75%, preferably less than 50%, and often less than 25%, 15%, 10%, 5%, 1% or even 0.1%, of the usual anti-inflammatory or analgesic dosage.

Minimum anti-inflammatory dosages for various NSAIDs are listed in Table 1, below:

TABLE 1

Minimum Anti-inflammatory Dosages for NSAIDs

| NSAID | Minimum Anti-inflammatory Dosage (mg) |
| --- | --- |
| Aspirin | 325[1] |
| Ibuprofen | 300[1] |
| Naproxen | 250[1] |
| Indomethacin | 25[1] |
| Piroxicam | 10[1] |
| Ketoprofen | 150[2] |
| Fenoprofen | 300[2] |
| Oxaprozin | 600[2] |
| Sulindac | 150[2] |
| Flurbiprofen | 50[2] |
| Etodolac | 200[2] |
| Diclofenac | 100[2] |
| Ketorolac | 5[2] |
| Tolmetin | 400[1] |
| Nabumetone | 500[1] |

[1] Physician's Desk Reference, 51st ed., Medical Economics Company, Inc.: Montvale, New Jersey (1997)
[2] Goodman and Gilman, The Pharmacological Basis of Therapeutics, 9th ed.

An especially preferred NSAID is aspirin. Aspirin preferably may be administered in daily dosages of at least 10 mg, more preferably at least 20, 40, 60, or 80 mg, but alternatively may be administered at levels of 100, 120, 140, 160, or up to 325 or 650 mg daily. Even higher daily dosages of aspirin may be consumed and will tend to suppress flushing in accordance with the invention, but these dosages run some risk of provoking undesirable side effects such as gastrointestinal (GI) upset or even ulceration. Moreover, these higher dosages are not more effective than the preferred lower dosages; indeed, because they tend to interfere with the metabolism of niacin in the liver, higher doses of aspirin tend to increase the serum concentration of niacin and thereby exacerbate the flushing reaction. An especially preferred daily dose range of aspirin is 40–80 mg, which is sufficient for extensive inhibition of synthesis of PGD2 in Langerhans cells, but low enough to have little capacity to provoke untoward side effects. Dosages at the low end of the range, e.g., 10–80 or 10–40 mg daily, may be administered even to many patients who are sensitive to aspirin and who readily develop GI ulcers, etc. Immediate release aspirin preferably is administered at least twice daily (i.e., bid), optionally three (tid) or four (qid) times daily. In particular preferred embodiments, an aspirin dose of 10–40 mg is administered twice a day.

However, in an even more preferred embodiment, the NSAID is administered as a sustained release formulation at least two hours prior to administering the antilipemic drug (e.g., niacin), preferably at least four hours prior, more preferably at least six hours prior, and most preferably about eight hours prior to administering the antilipemic drug. On the other hand, although predosing with a sustained release NSAID can be conducted for as long as is desired, for convenience, the NSAID is administered up to seven days prior to administering the antilipemic drug, preferably up to four days, more preferably up to 24 hours prior, and most preferably up to twelve hours prior to administering the antilipemic drug. If aspirin is used as the NSAID, the sustained release formulation is prepared such that, for example, a concentration from 3 to 100 mg of aspirin per hour is provided to the patient, preferably from 5 to 50 mg per hour and more preferably from 8 to 40 mg per hour. The most preferred dosage when aspirin is used is about 10 mg per hour.

Other preferred NSAIDs include ibuprofen, naproxen, phenylbutazone, and indomethacin. Dosages of these NSAIDs are sufficient to inhibit synthesis of PGD2 in skin macrophages (Langerhans cells), thereby decreasing the flush reaction. As with aspirin, these NSAIDs inhibit PGD2 synthesis in the skin at lower concentrations than are required for inhibition of synthesis of other PGs in nonskin tissue. For example, indomethacin is effective in reducing flush reaction at doses only 0.1%–10 % as great as those used for general anti-inflammatory effects.

Indomethacin is active in inhibiting flush in daily dosages as low as 2–25 mg, although up to 50, 100, 150, or even 200 mg daily may be taken. As with other NSAIDs, the daily dosage preferably is divided among 2, 3, 4, or more doses, or may be taken as one or more doses of a sustained release formulation. A preferred dosage range is 2–10 mg, including 2, 4, 5, 6, or 8 mg, preferably administered bid.

Ibuprofen is effective in inhibiting flush in a daily dosage range similar to that for aspirin, e.g., 5–160 mg, although higher doses are also effective. In certain embodiments, preferred daily dosages are 5–80 mg, often 10–50 mg, commonly 20–40 mg. The dosage usually is taken in a divided dose bid, tid, or qid.

Naproxen is active in suppressing flush at a daily dosage of as little as 5–100 mg, often within the range 10–80 mg, commonly 15–50 mg, typically 20–40 mg. As with other NSAIDs, multiple doses, e.g., bid, tid, or qid, are preferred. Higher dosages, e.g., within the usual anti-inflammatory dosage range of 500–1500 mg, are also effective but not required. Alternatively, a sustained release dosage form may be administered.

Phenylbutazone is active in suppressing flush at a daily dosage of 1–100 mg, often 5–50 mg, commonly 10–25 mg. As with other NSAIDs, multiple doses, e.g., bid, tid, or qid, are preferred. Higher dosages, e.g., within the usual anti-inflammatory dosage range of 300–600 mg, are also effective but not required. Dosages at the low end of the active range, e.g., 1–10 mg, are advantageous because of the incidence of side effects such as blood dyscrasias (e.g., granulocytosis, aplastic anemia). Alternatively, a sustained release dosage form may be administered.

Preferred single dose (i.e., immediate release) and sustained release dosage ranges for various NSAIDs are presented in Table 2, below:

TABLE 2

Preferred Dosage Ranges for NSAIDs

| NSAID | Single dose range (mg) | Sustained release range (mg/hr) |
|---|---|---|
| Aspirin | 10–160 | 3–100 |
| Ibuprofen | 5–160 | 5–50 |
| Naproxen | 5–100 | 5–50 |
| Indomethacin | 2–10 | 2–5 |
| Piroxicam | 1–10 | 1–5 |
| Ketoprofen | 50–100 | 5–50 |
| Fenoprofen | 10–50 | 10–50 |
| Oxaprozin | 50–100 | 10–50 |
| Sulindac | 5–100 | 5–50 |
| Flurbiprofen | 10–25 | 5–10 |
| Etodolac | 5–100 | 5–20 |
| Diclofenac | 5–50 | 5–20 |
| Ketorolac | 1–3 | 0.25–1 |
| Tolmetin | 20–200 | 5–50 |
| Nabumetone | 20–200 | 5–50 |

Preferred sustained release dosage ranges of NSAIDs for use in the invention are less than the minimum hourly non-inflammatory doses for NSAIDs. Sustained release dosage forms are currently commercially available for some, but not all, of the NSAIDs listed in Tables 1 and 2. For example, a timed release form of aspirin is available in tablet form from Glenbrook Laboratories; see, e.g., Physician's Desk Reference. The tablets contain aspirin in a microencapsulated formulation with guar gum, microcrystalline cellulose, and starch.

Other sustained release formulations may be prepared by conventional methods. Solid dosage forms such as tablets and capsules may be prepared by incorporating hydrophilic gums such as cellulose ethers, exemplified by methylcellulose, hydroxypropyl-methylcellulose, and sodium carboxymethylcellulose. These polymers control the release of an NSAID by diffusion out of and erosion of the gelatinous layer formed by hydration of the gum within the gut after oral administration. Sustained release tablets may be manufactured by direct compression of the mixture following blending or by conventional wet granulation methods. A blend comprising a polymeric gum, a diluent such as lactose, an NSAID, and a lubricant such as magnesium stearate may be mixed thoroughly (e.g., 30 minutes in a Hobart mixer) and compressed with a hydraulic press at pressures between 1,000–5,000 psi, resulting in a tablet having a hardness of 3–8 Kp. Capsules may be manufactured by filling shells with a similar blend. In general, the percentage of polymer may be varied between 20–80% (w/w).

A further aspect of the invention provides compositions for administering a flush inhibiting dose of an NSAID, and optionally, a carboxylic acid compound (other than the NSAID or a nicotinate) during the pretreatment period, as well as compositions for administering both (1) a flush-inhibiting dose of an NSAID and (optional) carboxylic acid compound, and (2) a flush-provoking dose of a nicotinate during the treatment period. Preferred compositions containing a flush-inhibiting dose of an NSAID and optional carboxylic acid compound (other than the NSAID or a nicotinate) provide a dose less than 15%, more commonly less than 10%, often less than 5%, and optionally as low as 1–0.1% of the usual anti-inflammatory dose of the NSAID. For example, in compositions wherein the NSAID is aspirin, an individual dose typically delivers 60 mg or less, often 40 mg or less, sometimes 10–20 mg or less of aspirin; by contrast, the usual anti-inflammatory single administration dose of aspirin for an adult is at least 325–650 mg, i.e., 1 or 2 conventional tablets of 325 mg each. Similarly, when the NSAID is ibuprofen, an individual dose of ibuprofen usually delivers 2–80 mg of ibuprofen, often 2–60 mg, frequently 5–40 mg, commonly 10–25 mg; by contrast, the usual anti-inflammatory dose is 300–600 mg. Where the NSAID is naproxen, an individual dose typically delivers 2–75 mg, often 5–50 mg, commonly 10–25 mg of naproxen; by contrast, the usual anti-inflammatory dose is 250–500 mg. Where the NSAID is indomethacin, an individual dose typically delivers 0.2–7.5 mg, often 0.5–5 mg, commonly 1–2.5 mg of naproxen; by contrast, the usual anti-inflammatory dose is 25–50 mg. The above single administration (individual) doses may be provided by one or multiple solid dosage units, e.g., one or two capsules or tablets may be needed to make up the total individual dose.

Similar doses of an NSAID component are preferred in pharmaceutical compositions of the invention comprising an NSAID, carboxylic acid compound (other than the NSAID or a nicotinate) and a nicotinate. These compositions permit a single dosage form, such as a tablet or capsule, to provide both a nicotinate and a flush-inhibiting amount of an NSAID and carboxylic acid compound (other than the NSAID or a nicotinate). Preferred compositions for co-administering a nicotinate, an NSAID and a carboxylic acid compound other than the NSAID or a nicotinate provide a single administration dose of NSAID which is 15% or less, more commonly 10% or less, often 5% or less, and optionally as low as 1–0.1% of the usual adult anti-inflammatory single dose. The single administration dose of the nicotinate preferably is at least 200 mg, more commonly 200–500 mg, often up to 500–750 mg, and optionally as high as 750–1,000 mg. The single administration dose may be provided in one or multiple tablets or capsules, as appropriate for convenience of patients. The combined dosage form ensures that patients will not forget to take the protective NSAID when they administer the nicotinate.

Pharmaceutical compositions comprising both an NSAID and a nicotinate necessarily will have a fixed ratio of NSAID to nicotinate. That ratio may be selected within broad limits, depending upon factors including the potency of the NSAID in inhibiting flush; the intended daily dosage of nicotinate; whether the dosage form is sustained release or immediate release with respect to each component; the presence and/or relative amount of a carboxylic acid compound other than the NSAID or nicotinate; and the number of doses to be administered per day. In analyzing these factors, a useful organizing principle is first to determine the total daily dosage of the NSAID, carboxylic acid compound and the nicotinate which a particular composition is intended to deliver, then to divide these dosages by the preferred number of administrations. For example, in certain preferred embodiments the daily dosage of nicotinic acid in immediate release formulations is 500–1500 mg. It the NSAID is selected to be immediate release aspirin, a daily dosage of, for example, 40–120 mg is within a portion of the broader range of dosages which are sufficient to inhibit flush. For convenience, administration twice daily (bid) is often a reasonable tradeoff between ease in patient compliance and attainment of steady serum levels of drug. Therefore, one might select, for example, a dosage form (e.g., capsule or tablet) comprising 250, 500, or 750 mg niacin and 20–60 mg aspirin. Obviously, many other possible choices may be made, and are consistent with the broad teachings of the invention.

A further aspect of the invention provides a combined dosage form comprising an immediate release niacin component and a sustained release NSAID component. This may be accomplished with either a bilayer tablet or a capsule containing immediate release granules of niacin and sustained release granules of an NSAID. Bilayer tablets may be manufactured by lightly pretamping a nicotinate layer deficient in or lacking a sustained release polymer, adding a layer containing an NSAID and a sustained release polymer, and compressing the combined powder as before. Optionally, the NSAID layer may further contain a carboxylic acid compound other than the NSAID or nicotinate.

In a further embodiment, the niacin component may be enterically coated. Enterically coated niacin may comprise either (a) granules of niacin or of a formulation comprising niacin, wherein the granules are individually enterically coated and compressed to form a tablet or a layer of a bilayer tablet, or (b) a tablet or layer thereof comprising niacin or a formulation containing niacin, in which the tablet or layer is coated with an enteric coating.

Enterically coated dosage forms do not dissolve or become absorbed by humans until they pass through the low pH environment of the stomach and pass into the relatively higher pH of the small intestine. Typical materials conventionally used as enteric coatings include, but are not limited to, cellulose acetate phthalate, polyvinylacetate phthalate, hydroxypropyl methylcellulose phthalate and methacrylic acid-methyl methacrylate copolymers. Such materials can be used individually or in combination. Additional formulating agents, such as plasticizers (e.g., one or more polyethylene glycols or propylene glycol) may be added to ensure physical strength and processability (e.g., to prevent cracking due to stress, low humidity or other factors).

Enterically coated niacin granules can be prepared in a fluid bed granulator by coating or agglomerating niacin powder with one or more enteric coating materials, such that microspheres or small particles of enterically coated niacin are formed. Alternatively, a whole tablet or capsule comprising niacin can be coated with the enteric coating materials.

Typically, the process comprises coating the dosage form with from one to five layers of enteric coating material (e.g., a methacrylate polymer such as EUDRAGIT S-100, available from Rohm), preferably by dipping the weighted tablet or capsule into a freshly prepared solution of the material for five seconds. The solution of enteric coating material(s) may be prepared by dissolving an appropriate amount of material in, e.g., 100 ml of a 4:6 mixture of acetone and isopropyl alcohol. After each immersion, the coating is allowed to dry in air, e.g., for 30 minutes prior to the next five-second immersion. A single coating is usually adequate to prevent the capsule or tablet from dissolving in the stomach. Alternatively, the granules, tablet or capsule may be coated or spray-dried in standard coating machines such as those typically employed in the pharmaceutical industry.

A preferred composition for administration of a dosage form containing an NSAID, a nicotinate, and optionally, a carboxylic acid compound (other than the NSAID or a nicotinate) is a kit comprising an individual or unit dose of the dosage form wherein each individual or unit dose is contained in a separate receptacle, such as a plastic or foil bubble pack, blister pack, or pouch. Optionally, a plurality of separate receptacles may be joined together into a combinatory structure such as a card, sheet, roll, or strip.

In certain embodiments, the dosage form comprises a single solid dosage form, such as a capsule or tablet, comprising a nicotinate, an NSAID (preferably a sustained release NSAID) and optional carboxylic acid compound other than the NSAID or nicotinate. In other embodiments, the kit comprises dual solid dosage forms, one containing either a sustained release NSAID or an NSAID and carboxylic acid compound other than the NSAID or nicotinate, and the other a nicotinate, both of which may be contained together in a single unit dose receptacle.

In a further alternative, the kit comprises three solid dosage forms, one containing an NSAID (which may be in a sustained release formulation), a second containing a carboxylic acid compound other than the NSAID or nicotinate, and the third containing a nicotinate, which may be contained together in a single unit dose receptacle, or which may be contained in separate receptacles (the NSAID and carboxylic acid compound may further be contained in a single receptacle, or in separate receptacles). In any of these alternative embodiments, the NSAID is preferably a sustained release NSAID.

In the solid dosage form, the unit dose contained in a receptacle may comprise one or a plurality of tablets or capsules of a given type. For example, where a single type of solid dosage form is employed, more than one such solid dosage form may be contained in a unit dose receptacle for administration as a single dose. Thus, two identical tablets, each comprising an NSAID and a carboxylic acid compound other than the NSAID or nicotinate, might be contained in a unit dose receptacle such as a single plastic blister, where both tablets are intended for simultaneous administration to a subject. The tablets may also each comprise an NSAID, a carboxylic acid compound (other than the NSAID or a nicotinate) and a nicotinate, contained in a unit dose receptacle such as a single plastic blister, where the tablets are intended for simultaneous administration to a subject. Two or more identical tablets or capsules per unit dose receptacle may be advantageous at higher doses of the nicotinate, since they can be kept small enough for ease in swallowing.

Another aspect of the invention provides for a flush-inhibiting unit dose of a sustained release NSAID or combination of NSAID and carboxylic acid compound (other than the NSAID or a nicotinate) which contains less than 15%, 10%, 5%, 1%, or 0.1% of the usual anti-inflammatory dose of that NSAID, wherein each unit dose is contained in a separate receptacle such as a plastic or foil bubble pack, blister pack, or pouch. Optionally, a plurality of such separate unit dose receptacles may be joined to form a combinatory structure such as a card, sheet, roll, or strip. These unit doses are convenient for providing a flush-inhibiting dose of NSAID and (optional) carboxylic acid compound (other than the NSAID or a nicotinate) during the pretreatment period. In some embodiments, a combinatory structure of sustained release NSAID or NSAID/carboxylic acid unit dose receptacles may be labeled, marked, or arranged so that the number of doses required for a pretreatment period is indicated on the combinatory structure.

For example, consider a situation in which two doses of sustained release NSAID or NSAID/carboxylic acid compound per day for a pretreatment period of three days were to be recommended. An appropriate combinatory structure might have receptacles organized, segregated, or marked off in groups of two, and numbered accordingly or labelled "AM" and "PM", etc. Three groups of two receptacles might be marked off and numbered consecutively to indicate the number of pretreatment days. A patient would then have a built-in means of keeping track of the pretreatment doses taken and would be able to determine when to begin administering treatment dosages.

A further aspect of the invention is a kit comprising both pretreatment and treatment compositions as described supra. In certain preferred embodiments, a kit comprises a combinatory structure containing (a) pretreatment unit dose(s) of an NSAID (preferably a sustained release NSAID) and optionally, a carboxylic acid compound (other than the NSAID or a nicotinate), and (b) a combinatory structure containing treatment unit doses of an NSAID, a nicotinate and optionally, a carboxylic acid compound other than the NSAID or nicotinate.

For convenience, the treatment and pretreatment combinatory structures should be readily distinguishable. For example, a card bearing pretreatment doses might be a different color or shape from a card bearing treatment doses. In general, the tablets or capsules themselves will differ in appearance between pretreatment and treatment pharmaceutical compositions, in addition to the distinguishing features of the combinatory structures containing the respective pharmaceutical compositions.

Clinical tests employing aspirin and niacin showed that the pretreatment phase can be shortened from 2 to 3 days with low dose immediate release aspirin to 2 to 8 hours with low dose sustained release aspirin. This may be significant improvement for patient compliance. A patient may take a sustained release NSAID or NSAID/carboxylic acid tablet in the morning, for example, then a niacin/NSAID or niacin/NSAID/carboxylic acid tablet in the afternoon. From that point on, as long as niacin and the NSAID or NSAID/carboxylic acid compound are taken together (preferably sustained release NSAID), the side effect of severe flushing will be significantly diminished or completely eliminated.

Sustained release aspirin appears to be more effective at cumulatively suppressing the production of prostaglandin D2 and maintaining this suppression, as evidenced by more effective suppression of flushing. The clinical results of the study in Example 7 below support this conclusion.

Thus, the present kit may comprise either of the two following embodiments. The first embodiment may comprise (a) a predosing sustained release NSAID (preferably aspirin) component and (b) a combination sustained release NSAID/immediate release niacin formulation component, in the same package. Each component may be in the same dosage form (tablet or capsule). Alternatively, the present kit may comprise a predosing sustained release NSAID package and a separate package combining sustained release NSAID and immediate release niacin in the same dosage form.

In these embodiments of the kit and method, the sustained release NSAID may be present in a formulation providing metered doses within the sustained release ranges stated above for each NSAID. For example, if aspirin is used, the aspirin may be present in a formulation providing metered doses of 10 mg per hour to 100 mg of aspirin per hour, administered from 2 hours to 24 hours before administering a flush-producing amount of niacin. Preferably, the amount of aspirin is from about 20 mg to about 50 mg per hour for at least four hours prior to dosing with niacin. The sustained release NSAID is preferably delivered over an 8–10 hour period.

The combined niacin-NSAID formulation, for example, may be a bilayer tablet where one of the layers is sustained release NSAID, and the other layer is immediate release niacin, as described above and in application Ser. Nos. 08/425,057 and 08/425,060 (both of which are incorporated herein by reference in their entireties). Alternatively, the niacin-NSAID formulation may be a bilayer tablet where the first (and in a further embodiment, inner) layer may be an enterically coated immediate release or sustained release niacin and the second (or outer) layer is immediate release or sustained release NSAID (which may further contain a carboxylic acid compound other than aspirin or niacin).

The enteric coating is designed to protect the niacin from being released into the patient's bloodstream until after the enterically coated bilayer formulation passes through the patient's stomach into the small intestine, at which time the niacin is released as a bolus. Enteric coatings for use in the present invention can be prepared in accordance with known methods.

Delayed release formulations, such as those having enteric coatings, may also be prepared by mixing niacin with appropriate excipients (such as maize starch) and the enteric material, then tableting the mixture. If, for example, the enterically coated niacin is one layer of a bilayer tablet, the enteric coated portion may be tamped into the chamber first, then compressed, and the NSAID-containing portion may be compressed on top of the previously compressed layer. Alternatively, if niacin particles are employed and are previously coated, the NSAID and coated niacin particles may simply be mixed, then either encapsulated or tableted together in a single formulation.

In a further alternative embodiment, the antilipemic drug-NSAID formulation may comprise two tablets (which may be administered concurrently), where one tablet is an enterically coated immediate release or sustained release antilipemic drug (niacin), and the other tablet contains one or more immediate release or sustained release NSAID, and optionally, a carboxylic acid compound other than the NSAID or antilipemic drug. In a further embodiment of the method for suppressing cutaneous erythema and of treating hyperlipemia, the patient is given a predose of NSAID which includes a major proportion of a sustained release NSAID which can be formulated as described, and a minor proportion of an immediate release form of the NSAID which can be in the conventional form. The immediate release form quickly raises the level of NSAID to an effective level and the sustained release portion maintains the effective level. With this combination, the predosing period is greatly reduced, and in many instances, the predosing and administration of the antilipemic drug can be accomplished the same day without flushing. When the NSAID is aspirin, for example, the immediate release portion can be from 20 to 80 mg per unit dose and the sustained release dosage formulation can be an amount which will release from 3 to 100 mg per hour of aspirin. Sustained release dosage ranges for other NSAIDs are listed in Table 2, above.

Consequently, the present methods of suppressing cutaneous erythema and of treating hyperlipemia may comprise administering to a patient in need thereof a composition which provides an effective amount of an NSAID, which may be sustained release and/or combined with a carboxylic acid compound other than the NSAID or the antilipemic drug, effective to reduce cutaneous erythema caused by the antilipemic drug for at least 2 hours prior to release of the antilipemic drug in, or absorption of the antilipemic drug by, the patient.

Since niacin is usually taken BID or TID, the sustained release NSAID may provide an overlap in NSAID PGD-2 suppression in the event of a missed dose. Thus, even if a patient misses a day altogether, the patient still benefits from the previous day's NSAID suppression.

Thus, the present invention concerns a method of suppressing cutaneous erythema in a patient to whom an antilipemic drug is to be administered, comprising administering to the patient an amount of a sustained release nonsteroidal anti-inflammatory drug (NSAID) effective to reduce the cutaneous erythema at least 2 hours prior to administering the antilipemic drug to the patient. In a preferred embodiment, the NSAID and the carboxylic acid compound are administered from 2 hours to 7 days prior to administering the antilipemic drug, more preferably from 2 to 24 hours prior to administering the antilipemic drug, and even more preferably from 4 to 12 hours prior to administering the antilipemic drug. In further preferred embodiments of the method, the NSAID is administered in an amount providing an amount per hour within the sustained release dosage range provided in Table 2, above, for each NSAID.

In addition, the present invention also concerns a method of suppressing cutaneous erythema in a patient to whom an antilipemic drug is to be administered, comprising administering to the patient an amount of (a) a nonsteroidal anti-inflammatory drug (NSAID) and (b) a carboxylic acid compound other than the NSAID or the antilipemic drug effective to reduce the cutaneous erythema prior to administering the antilipemic drug to the patient. Similarly, in preferred embodiments, the NSAID and the carboxylic acid compound are administered at least 2 hours prior to administering the antilipemic drug, more preferably from 2 hours to 7 days prior to administering the antilipemic drug, even more preferably from 2 hours to 4 days prior to administering the antilipemic drug, and most preferably from 2 to 24 hours prior to administering the antilipemic drug; the NSAID may be aspirin, may be administered in an amount of from 10 to 40 mg from 2 to 4 times daily, or may be in a sustained release formulation providing a sustained release dosage of NSAID within the sustained release dosage range provided in Table 2, above, for each NSAID. In a further preferred embodiment, the carboxylic acid compound is citric acid.

The present invention also concerns a method of treating hyperlipemia comprising administering to a patient in need of an antilipemic drug an amount of a sustained release nonsteroidal anti-inflammatory drug (NSAID) effective to reduce cutaneous erythema which the antilipemic drug causes in the patient, and at least 2 hours after administering the NSAID, administering an effective amount of the antilipemic drug to treat the hyperlipemia. In preferred embodiments of this method, the NSAID is in a formulation providing an amount within the sustained release dosage range provided in Table 2, above, for each NSAID, and the antilipemic drug is niacin.

The present invention alternatively concerns a method of treating hyperlipemia comprising administering to a patient in need thereof an antilipemic drug, a nonsteroidal anti-inflammatory drug (NSAID), and a carboxylic acid compound other than NSAID or the antilipemic drug, wherein the NSAID and the carboxylic acid compound are administered in an amount effective to reduce cutaneous erythema which the antilipemic drug causes in the patient, and the antilipemic drug is administered in an amount of effective to treat the hyperlipemia.

In preferred embodiments of this method, the NSAID is in a sustained release formulation providing an amount within the sustained release dosage range provided in Table 2, above, for each NSAID; and/or the carboxylic acid compound is citric acid, administered in an amount of from 50 to 500 mg; and/or the antilipemic drug is niacin.

Alternatively, the NSAID is aspirin and the aspirin is administered in an amount of from 10 to 40 mg from 2 to 4 times daily.

Furthermore, as described above, inclusion of a carboxylic acid other than, for example, an NSAID and niacin in a composition containing an antilipemic drug and an NSAID is expected to further improve the reduction in the flushing effect caused by the antilipemic drug. Thus, the present invention concerns a composition for reducing the flushing effect (cutaneous erythema) caused by an antilipemic drug such as niacin, comprising (a) a sustained release NSAID; and
(b) a carboxylic acid compound other than component (a) or an antilipemic drug such as niacin, preferably citric acid, wherein components (a) and (b) are present in an amount effective to reduce flushing caused by an antilipemic dosage of the antilipemic drug.

Preferably, the amount of components (a) and (b) combined is effective to reduce flushing (cutaneous erythema) in at least half of a statistically significant group of subjects (e.g., a group of at least 4 subjects, preferably 6 subjects, and more preferably 12 subjects) or is effective to reduce overall flushing in such a group of subjects by at least 75%, preferably at least 80%, and more preferably at least 85%, as measured by a decrease in skin temperature relative to a group of the same size administered the same amount of antilipemic drug alone.

In further preferred embodiments of the composition, the antilipemic drug is niacin, the carboxylic acid compound is citric acid, and the composition provides an amount of NSAID per hour to the patient within the sustained release dosage range provided in Table 2, above, for each NSAID.

The present invention also concerns a composition for treating hyperlipemia comprising the present composition for reducing flushing in combination with an antilipemic amount of an antilipemic drug, preferably niacin. Thus, the composition for treating hyperlipemia may comprise an effective amount of an antilipemic drug to treat the hyperlipemia, a nonsteroidal anti-inflammatory drug (NSAID), and a carboxylic acid compound other than the NSAID or the antilipemic drug, wherein the NSAID and the carboxylic acid compound are present in a combined amount effective to reduce flushing caused by the effective amount of the antilipemic drug.

In preferred embodiments of this composition, the antilipemic drug is niacin, the carboxylic acid compound is citric acid, and the composition may provide a sustained release of NSAID to the patient in an amount within the sustained release dosage mage provided in Table 2, above, for each NSAID.

The present invention also concerns a kit for treating hyperlipemia comprising at least one pre-dosage unit containing the present composition for reducing flushing caused by an antilipemic drug and at least one dosage unit of an antilipemic drug, preferably niacin, effective to treat hyperlipemia. The dosage unit may further comprise an NSAID and a carboxylic acid compound (preferably citric acid) in an amount effective to suppress or inhibit the flushing caused by the antilipemic drug. Any of the formulations described above may be used in the present composition or in the pre-dosage or dosage units of the present kit.

The present invention also concerns a kit for treating hyperlipemia comprising at least one unit dosage comprising an effective amount of an antilipemic drug to treat hyperlipemia, and at least one unit pre-dosage of a sustained NSAID effective to prevent or inhibit cutaneous erythema caused by the antilipemic drug.

In preferred embodiments of the kit, the unit dosage further comprises an amount of the NSAID effective to maintain suppression of the cutaneous erythema; the antilipemic drug may be niacin or a congener thereof; and the unit pre-dosage may provide an amount of NSAID to the patient within the sustained release dosage range provided in Table 2, above, for each NSAID.

The present invention may also concern a kit for treating hyperlipemia comprising at least one unit dosage comprising an effective amount of an antilipemic drug to treat hyperlipemia and at least one unit pre-dosage of NSAID and a carboxylic acid compound other than the NSAID or the antilipemic drug effective to prevent or inhibit cutaneous erythema caused by the antilipemic drug.

In preferred embodiments of this kit, the unit dosage may further comprise an amount of the NSAID and the carboxylic acid compound effective to maintain suppression of the cutaneous erythema; the antilipemic drug may be niacin or a congener thereof; the unit pre-dosage may be a sustained release formulation providing an amount of NSAID per hour to the patient within the sustained release dosage range provided in Table 2, above, for each NSAID; and the carboxylic acid compound is citric acid.

The present invention also concerns the use of niacin or a congener thereof to increase the effectiveness of an NSAID such as aspirin for anti-platelet aggregation in non-responders. Nicotinic acid is a carboxylic acid and, therefore, when combined with an NSAID such as aspirin, nicotinic acid should increase the effectiveness of the NSAID in non-responders.

In this case, the purpose of the invention is to increase the effectiveness of NSAIDs such as aspirin in non-responders, rather than to reduce the side effects of the niacin. Niacin itself does not exhibit any anti-platelet aggregating effects, but when combined with aspirin, helps to increase aspirin's effectiveness in non-responders. Thus, the present invention concerns a composition for inhibiting or preventing platelet aggregation (for example, for treating thrombosis) comprising (a) an NSAID, preferably aspirin;
(b) niacin and/or a congener thereof (hereinafter, referred to collectively as "niacin"); and
(c) optionally, a carboxylic acid other than components (a) and (b), wherein the combined components (a), (b) and (c) are present in an amount effective to inhibit aggregation of platelets or to treat thrombosis. Preferably, the composition is formulated for use in a patient who does not respond to anti-platelet aggregation or thrombosis therapy using an NSAID alone. The NSAID is typically present in an amount effective to treat thrombosis or exhibit anti-platelet aggregation activity in a patient who responds to NSAID therapy for the treatment of thrombosis. The niacin and (optional) carboxylic acid are present in amounts effective to increase the anti-platelet aggregation activity of the NSAID in a non-responding patient, and/or to increase the effectiveness of the NSAID in a patient in need of treatment for thrombosis.

The ranges of components in this composition may be as shown in Table 3 below:

TABLE 3

|  | General Range | Preferred | Most Preferred |
| --- | --- | --- | --- |
| Niacin | 50–5000 mg | 250–750 mg | 500 mg |
| Aspirin | 50–1000 mg | 50–100 mg | 50 mg |
| Carboxylic Acid | 50–500 mg | 100–200 mg | 100 mg |

The above individual dosage forms may be administered in a kit comprising two tablets or capsules for administration BID or TID, and the aspirin part of the formula may be sustained release as described above (in a bilayer tablet, for example). The composition may also contain another carboxylic acid, such as citric acid, as either an individual component (tablet, capsule, "gelcap", etc.) or in a combined formulation with one or both of the NSAID and niacin.

The present invention also concerns a method of inhibiting platelet aggregation or of treating thrombosis comprising administering an effective amount of a composition comprising (a) an NSAID, preferably aspirin, (b) niacin or a congener thereof, preferably niacin, and optionally, (c) a carboxylic acid other than components (a) and (b), preferably citric acid, to a patient in need thereof. Preferably, the patient is one who does not respond to anti-platelet aggregation therapy or therapy for thrombosis using an NSAID (such as aspirin) alone.

The present invention also concerns a method of increasing the effectiveness of a nonsteroidal anti-inflammatory drug (NSAID) in inhibiting or preventing platelet aggregation, in vitro or in vivo, comprising co-administering to a medium containing platelets or to a patient an amount of (a) niacin and/or a congener thereof and (b) a carboxylic acid compound other than niacin and/or a congener thereof effective to increase the anti-platelet aggregating activity of the NSAID. Specific ranges of amounts, times and methods of administration, suitable media, etc., are as described herein or as known to those of ordinary skill in the art to which the invention belongs.

Carboxylic acids other than niacin useful in the present invention include physiologically tolerated carboxylic acids. Preferably, the carboxylic acid contains (a) from 2 to 12 carbon atoms, and (b) at least one carboxylic acid group and at least one hydroxy, amino, keto, aldehyde and/or ester group, or alternatively, two or more carboxylic acid groups. Examples of such carboxylic acids include succinic acid, lactic acid, pyruvic acid, fumaric acid, malic acid, maleic acid, adipic acid, ascorbic acid, o-phthalic acid, m-phthalic acid, p-phthalic acid, glutaric acid, glucuronic acid, glutamic acid, aspartic acid, 1,2-cyclohexanedicarboxylic acid, 1,2-cyclohexenedicarboxylic acid, 4,5-cyclohexenedicarboxylic acid, malonic acid, oxalic acid and derivatives thereof (e.g., substituted with one or more lower alkyl groups, halogen atoms, lower alkoxy groups, etc.; pharmaceutically acceptable salts thereof; lower alkyl (i.e., C1–C6) esters thereof; etc.).

The following examples are illustrative of certain aspects of the invention and are not to be construed as limiting the scope of the invention as a whole.

EXAMPLE 1

Pretreatment with Single Dose Aspirin

Three subjects were administered 40 mg of aspirin 1 hour prior to a single 500 mg dose of immediate release nicotinic acid (Squibb). All three experienced severe flushing with a sunburned appearance on the face and ears and blotches on the palms. All reported a subjective sensation of cutaneous warmth. Urine samples obtained at intervals after niacin administration demonstrated excretion of significant amounts of PGD-M, the major urinary metabolite of PGD2, over the next 7 hours (FIG. 1), confirming the association between PGD2 release and flushing symptoms.

Figure 2:
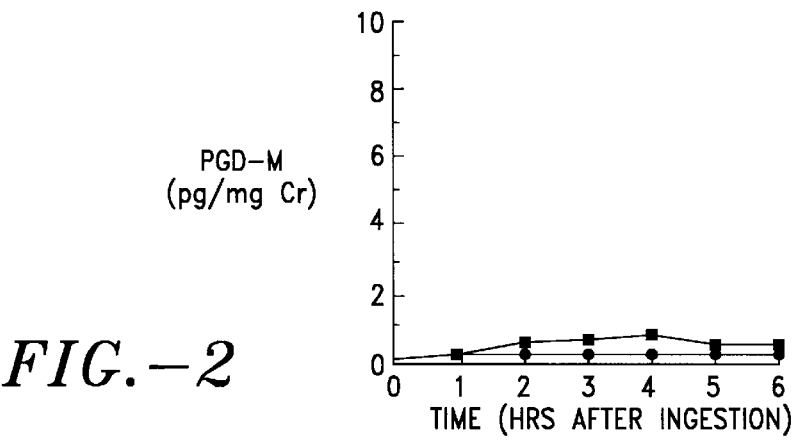
FIG. 2 is a graph showing the effect of 3 days of pretreatment with 40 mg aspirin on the excretion of PDG-M in human subjects following ingestion of 500 mg nicotinic acid.
Figure 3:
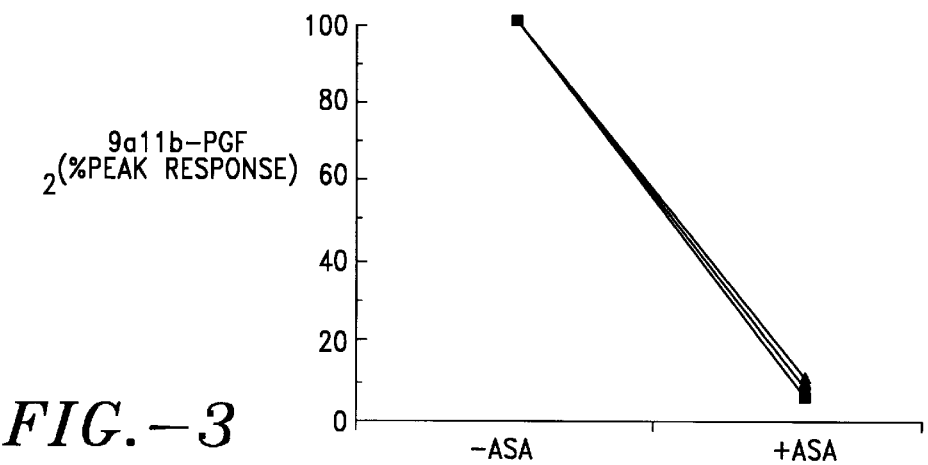
FIG. 3 is a graph showing the percent inhibition, with (B) or without (A) pretreatment with 40 mg aspirin, of PG release following topical application of nicotinic acid.

Two weeks later, the same subjects were administered 40 of mg aspirin for each of four days. On the fourth day, a single 500 mg dose of immediate release nicotinic acid (Squibb) was administered 1 hour after the aspirin. Two of the subjects experienced virtually no flushing. The third subject experienced some flushing, but less than that encountered previously without multi-day aspirin pretreatment. Urinary excretion of PGD-M was much lower (FIG. 2), confirming the suppressive activity of aspirin on PGD2 release. Release of PGF2 after aspirin pretreatment (40 mg) was approximately 10% of baseline (FIG. 3).

EXAMPLE 2

Pretreatment with Bid Aspirin

Three subjects were administered 40 mg of aspirin twice daily (i.e., bid) in the morning and evening for three days. On the fourth day, a 500 mg dose of immediate release nicotinic acid was taken with 40 mg aspirin. None of the subjects experienced any appreciable flushing.

Two weeks later the same subjects were administered a single dose of 500 mg of nicotinic acid without aspirin. All three experienced severe flushing.

EXAMPLE 3

Inhibition of PG Release in Vitro

Figure 4:
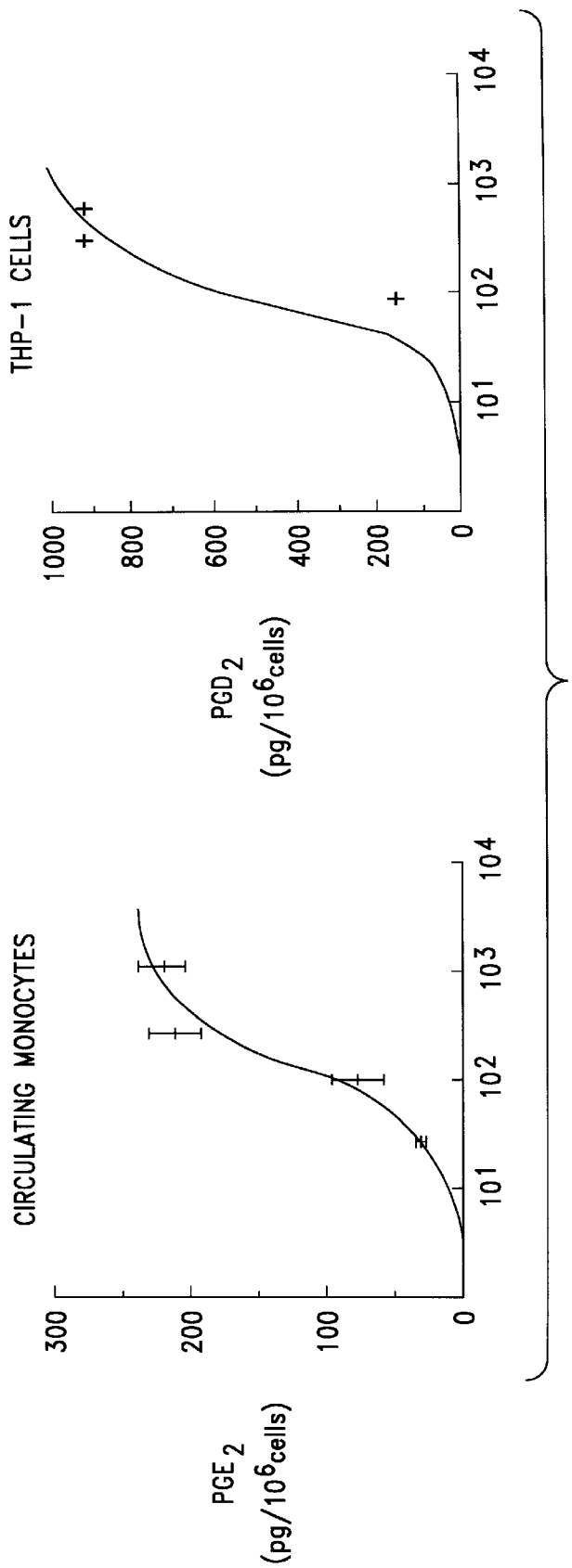
FIG. 4 is a graph showing the increase in release of PGE2 from circulating monocytes (panel A) and of PGD2 from cultured THP-1 cells (panel B) versus nicotinic acid concentration.

Niacin was shown to stimulate in vitro release of PGs from human circulating monocytes, which are precursors of macrophages, and from the human macrophage cell line THP-1 (FIG. 4). Aspirin in vitro inhibited niacin-stimulated release of PG from THP-1 cells with an IC50 of circa 0.38 micromolar (0.07 mg/ml) (FIG. 5). By comparison, a dose of 40 mg of aspirin in an adult causes a peak plasma concentration of about 0.6 mg/ml. Thus, the in vitro results are consistent with the clinical observation of inhibition of flushing with 40 mg of aspirin.

EXAMPLE 4

Inhibition of PG Release from Kupfer Cells in vitro

Kupfer cells, a type of macrophage found in the liver, were obtained from guinea pigs. Niacin stimulated release of PGD2 from Kupfer cells in vitro in a dose-dependent manner (FIG. 6). This further supports the conclusion that macrophages are the source of PGs released by niacin administration in vivo.

EXAMPLE 5

Niacin-stimulated Release of PG from Skin

Figure 7:
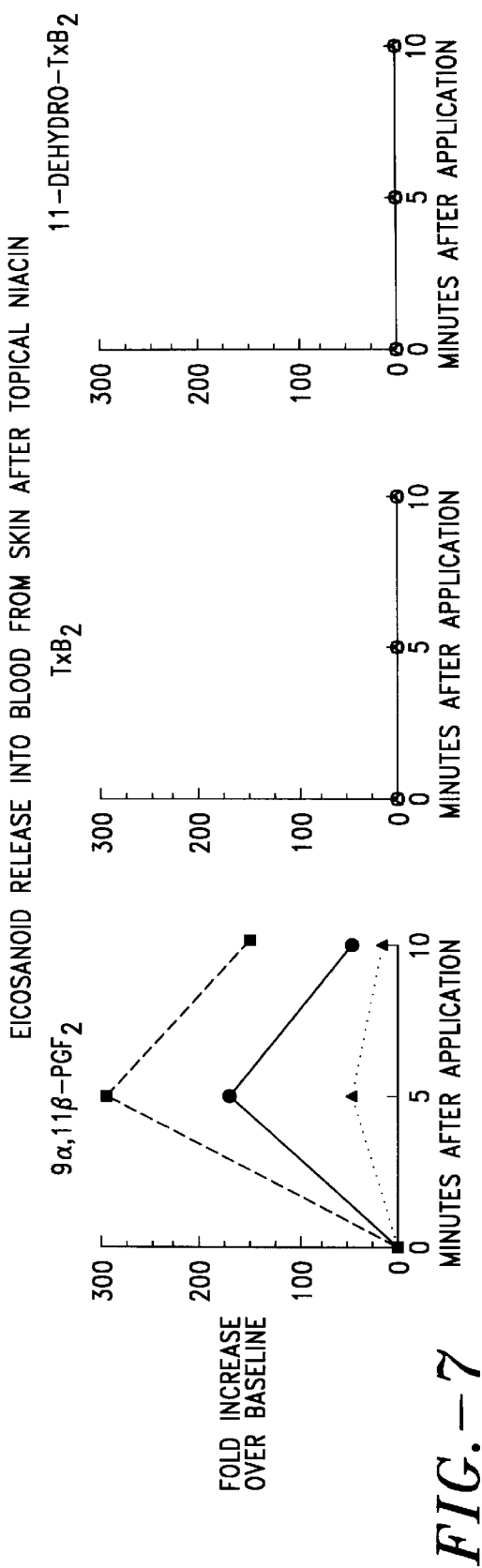
FIG. 7 is a graph showing release of eicosanoids into blood coming from the skin versus time after topical application of nicotinic acid; eicosanoids measured are 9a, 11b-PGF2 (panel A), TxB2 (panel B), and 11-dehydro-TxB2 (panel C).
Figure 8:
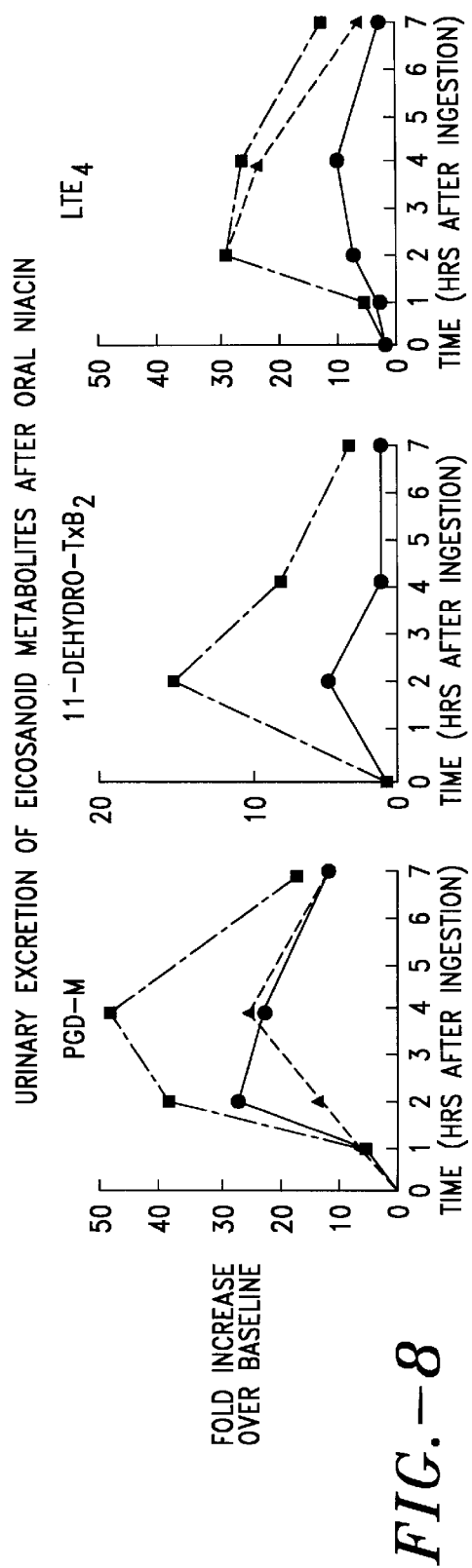
FIG. 8 is a graph showing urinary excretion of eicosanoid metabolites versus time after oral administration of nicotinic acid; eicosanoids measured are PGD-M (panel A), 11-dehydro-TxB2 (panel B), and LTE4 (panel C).

As further evidence that niacin-induced skin flushing is mediated by release of PGs, skin was treated with topical niacin and release of eicosanoids into the efferent circulation was measured. Niacin increased the release of 9a, 11b-PGF2, a metabolite of PGD2, but did not release another eicosanoid, thromboxane (TxB2), which is also found in macrophages (FIG. 7). However, oral administration did result in increased amounts of metabolites of thromboxane and leukotriene, as well as PGD2, in urine (FIG. 8). Langerhans cells, the macrophages of skin, may differ from other macrophages in releasing lesser amounts of eicosanoids other than PGD2.

EXAMPLE 6

Pretreatment with Indomethacin in vitro

Indomethacin was used in place of aspirin to inhibit PG production in THP-1 cells in vitro as in Example 3. The IC50 was calculated to be approximately 1 nM. By contrast, inhibitory concentrations of indomethacin on PG production in other cell types are in the micromolar range. Thus THP-1 cells are approximately 1000 times more sensitive to indomethacin than are other cells. The dose of indomethacin required for in vivo inhibition of flushing is expected to be quite low as well. This confirms that low doses of NSAIDs other than aspirin are also effective in alleviating niacin-induced flushing.

EXAMPLE 7

Pretreatment with Sustained Release Aspirin

Three subjects were given a sustained release aspirin formula containing 325 mg of aspirin which released all of the aspirin over an 8-hour period (40 mg per hour). Six hours later, they were each given 500 mg of immediate release niacin with 40 mg of immediate release aspirin. All three subjects experienced no flushing whatsoever. All subjects had not taken any niacin for at least one month prior to this study, and had never previously taken high dose niacin for cholesterol reduction.

Two weeks later, the same subjects were given 500 mg of immediate release niacin without any predosing or concurrent dosing with aspirin. All three subjects experienced severe flushing.

Two weeks later, the same subjects were given 325 mg of aspirin ½ hour before dosing with 500 mg of immediate release niacin, as is the customary practice (see *J. Fam. Pract.* 34:165–168 (1992)). Two subjects experienced flushing, though slightly diminished, and the third subject experienced severe flushing. All three subjects experienced significantly greater side effects from the niacin than they did when they had predosed with the sustained release aspirin for 6 hours.

After another two weeks, the three subjects were given the same sustained release aspirin formula that released 40 mg per hour over an 8 hour period (325 mg). Six hours later, all three subjects were given 500 mg of immediate release niacin without any additional aspirin. None of the subjects experienced any flushing, indicating that the predose sustained release aspirin was probably still active in suppressing prostaglandin D2 production. This indicates that concurrent dosing with aspirin is not necessary as long as there is enough aspirin still being released from the sustained release aspirin formula to suppress PGD2 release and/or formation.

EXAMPLE 8

Niacin Flushing/Pharmacokinetic Study

This study was conducted at a major university hospital to measure the difference in flushing between (1) pretreatment bid with 81 mg of aspirin for three days prior to combined aspirin/niacin dosing on the fourth day, and (2) immediate release niacin (Squibb) without aspirin. Fourteen healthy male subjects completed the study. After randomization, subjects were given a placebo or 81 mg of aspirin bid for three days. The study was double-blind.

On the fourth day, following a standardized breakfast and lunch, the subjects received either a single 500 mg oral dose of nicotinic acid with 81 mg of aspirin or a matching dose of commercially available immediate release niacin without aspirin. Room temperature and humidity were constant during the trial.

Flushing was measured in three ways: (1) quantitatively using laser Doppler, (2) subjectively via questionnaire, and (3) by measuring a biochemical marker of flushing, a stable metabolite of prostaglandin D2. Complete pharmacokinetic parameters in timed blood samples after oral administration were also measured in plasma and urine. Flushing, as measured by continuous and simultaneous recording of cutaneous blood flow on each side of the neck using laser Doppler techniques (Moor Instruments), provides an arbitrary representation of cutaneous blood flow defined as FLUX. Flux is expressed in arbitrary units (AU) from baseline (FLUXpeak-FLUXbaseline; see FIG. 11B). Duration of flush is the time in minutes from the beginning to the end of Flux shift in the DRTSOFT plot. The AUC (area under the curve) of the flux was calculated, and the mean AUC is shown in FIG. 11A.

In this study, the novel aspirin predosing regimen and aspirin/niacin formulation resulted in a significant decrease in the severity and duration of flushing when compared to administration of commercially available immediate release niacin alone. The severity of flushing, as estimated by shift of flux from baseline (i.e., change in the skin blood flow), was reduced by approximately 70% (see FIG. 10A). Flushing was completely eliminated in 6 subjects and reduced markedly in the rest of the subjects receiving the aspirin predosing regimen and combined aspirin/niacin formulation (see Table 3 above).

The effect of the novel predosing regimen and formulation on flushing duration was marked. The duration of flushing was reduced from 41.6±18 minutes to 15.8±16 minutes (65% reduction [p=0.002]; see FIG. 10C). The temperature rise associated with flushing was also reduced. FIG. 10B shows that skin temperature rises twice as much with placebo (immediate release niacin) than with aspirin/niacin.

From close observation of the characteristics of the flushing, the new NSAID predosing regimen and NSAID/niacin formulation reduce the local intensity of the flushing, and also appear to reduce the extent of body area affected.

TABLE 4

Effects of Aspirin vs. Placebo on Flushing Induced by Nicotinic Acid

|  | Placebo | Aspirin | |
|---|---|---|---|
| $AUC_{flux}$ | 9572.3 + 5310 | 3022.5 + 2772 | p = 0.0001* |
| Flushing duration | 41.6 ± 18 | 15.8 ± 16 | p = 0.002* |
| Local T° change ° C. | 1.36 ± 0.85 | 0.61 ± 0.56 | p = 0.016* |

Values given represent the mean ± S.D.; n = 14.
*: Determined by the paired t-test.

TABLE 5

Rating of Flushing by Subject

|  | Placebo | Aspirin |
|---|---|---|
| None | 1 | 6 |
| Mild | 0 | 4 |
| Moderate | 1 | 1 |
| Severe | 8 | 3 |
| Very severe | 4 | 0 | p < 0.05 (Wilcoxon Matched-Pairs test); n = 14

TABLE 6

Rating of Flushing by Investigator

|  | Placebo | Aspirin |
|---|---|---|
| None | 1 | 8 |
| Mild | 0 | 2 |
| Moderate | 2 | 3 |
| Severe | 8 | 1 |
| Very severe | 3 | 0 | p < 0.05 (Wilcoxon Matched-Pairs test); n = 14

EXAMPLE 9

Mixed Sustained and Immediate Release Aspirin

In this study, the effect and duration of action of pretreatment is evidenced with a combination of 350 mg of sustained release aspirin (SRA) and 80 mg of immediate release aspirin (IRA) given four hours prior to dosing with a single dose of 500 mg of niacin and 80 mg of IRA for the prevention of the flushing reaction due to the niacin.

The study is a one-day randomized, double-blind, placebo-controlled, parallel treatment with 20 subjects (10 subjects per treatment group) and with 2 treatment groups.

TABLE 7

| Group | Treatment | | |
|---|---|---|---|
| | -4 Hours | 0 Hours | 8 Hours |
| Placebo | Placebo | Niacin + Placebo | Niacin |
| Active | SRA = 350 mg IRA = 80 mg | Niacin + 80 mg IRA | Niacin |

All subjects are pre-treated with placebo or the combination of IRA and SRA four hours prior to dosing with either a single dose of 500 mg niacin or niacin+80 mg of IRA. The initial dosing of niacin occurs in the fed state. After dosing with niacin, flushing is assessed by the grading (none, mild, moderate, severe, very severe) of the severity of facial flushing by the subject and by designated study personnel. After 8 hours, each subject is dosed with 500 mg of niacin and the severity of facial flushing reassessed.

To evaluate the pharmocokinetics of niacin and aspirin (ASA) and niacin, blood samples will be drawn at the following schedule: 0, 5, 15, 30, 45 minutes and 1, 2, 3, 4, 5, 6, 7 and 8 hours after the initial dosing with ASA for ASA levels, and at 0, 20, 45 minutes and 1, 1.5, 2, 2.5, 3, 4, and 6 hours after the initial dosing with niacin for niacin levels.

EXAMPLE 10

Resistant Patient Study

This study is evaluated when flushing does not occur after the initial dose of niacin, but does occur at the 8-hour point.

The study is designed to evaluate the dose response and duration of action of pretreatment with placebo and various combined doses of SRA and IRA given four hours prior to dosing with a single dose of 500 mg of niacin and various combined doses of SRA and IRA for the prevention of the flushing reaction due to the niacin. The secondary objective is to determine the pharmacokinetics of the different doses of ASA and niacin.

The study is 6 one-day randomized, double-blinded, placebo-controlled, parallel treatment with 60 subjects (10 subjects per treatment group) in 6 treatment groups.

TABLE 8

| | Treatment (mg) | | | | | | | | |
|---|---|---|---|---|---|---|---|---|---|
| | -4 Hours | | | 0 Hours | | | 8 Hours | | |
| Group | IRA | SRA | Niacin | IRA | SRA | Niacin | IRA | SRA | Niacin |
| Placebo | 0 | 0 | 0 | 0 | 0 | 500 | 0 | 0 | 500 |
| Active | 40 | 80 | 0 | 40 | 80 | 500 | 0 | 0 | 500 |
| | 80 | 80 | 0 | 80 | 80 | 500 | 0 | 0 | 500 |
| | 80 | 150 | 0 | 80 | 160 | 500 | 0 | 0 | 500 |
| | 80 | 240 | 0 | 80 | 240 | 500 | 0 | 0 | 500 |
| | 80 | 320 | 0 | 80 | 320 | 500 | 0 | 0 | 500 |

All subjects are pretreated with placebo or the various doses of ASA four hours prior to dosing with a single dose of 500 mg niacin plus various combinations of IRA. The initial dosing of niacin occurs in the fed state. After dosing with the niacin, flushing is assessed by the grading (none, mild, moderate, severe, very severe) of the severity of facial flushing by the subject and by a designated study personnel. After 8 hours, each subject is dosed with 500 mg of niacin and the severity of facial flushing reassessed.

To evaluate the pharmacokinetics of ASA and niacin blood samples are at the following schedule: 0, 5, 15, 30, 45 minutes and 1, 2, 3, 4, 5, 6, 7, and 8 hours after each dosing with ASA for ASA levels and at 0, 20, 45, minutes and 1, 1.5, 2, 2.5, 3, 4, and 6 hours after dosing with niacin for niacin levels.

Obviously, numerous modifications and variations of the present invention are possible in light of the above teachings. It is therefore to be understood that, within the scope of the appended claims, the invention may be practiced otherwise than as specifically described herein.

All publications and patent applications mentioned herein are hereby explicitly incorporated herein by reference.

The invention claimed is:

1. A pharmaceutical composition for administration of hypolipemic amounts of niacin having reduced capacity to provoke a flushing reaction in a subject, comprising
   (1) a hypolipemic amount of niacin, and
   (2) a nonsteroidal anti-inflammatory drug (NSAID),
      wherein the NSAID is a member selected from the group consisting of aspirin, ibuprofen, indomethacin, phenylbutazone, and naproxen, and
      wherein the NSAID is present in an amount effective to reduce cutaneous flushing caused by the niacin, and
      wherein the NSAID is present in an amount up to the amount shown below for that member.

| | |
|---|---|
| Aspirin | 160 mg |
| Ibuprofen | 160 mg |
| Indomethacin | 10 mg |
| Phenylbutazone | 100 mg |
| Naproxen | 100 mg. |

2. The composition of claim 1, wherein the amount of niacin is 50 mg–2 g.

3. The composition of claim 2, wherein the amount of niacin is 500 mg–2 g.

4. The composition of claim 1, wherein the NSAID is in immediate release dosage form.

5. The composition of claim 1, wherein the NSAID is in sustained release dosage form.

6. A method of suppressing cutaneous erythema in a patient to whom niacin is administered, comprising administering to said patient an amount of
   (a) a nonsteroidal anti-inflammatory drug (NSAID), and
   (b) a carboxylic acid compound other than said NSAID or niacin effective to reduce said cutaneous erythema prior to niacin being administered to, released in or absorbed by said patient,
      wherein said NSAID is a member selected from the group consisting of aspirin, ibuprofen, indomethacin, phenylbutazone, and naproxen, and
      wherein said NSAID is administered in an amount within the following range for that member:

| | |
|---|---|
| Aspirin | 10–160 mg |
| Ibuprofen | 5–160 mg |
| Indomethacin | 2–10 mg |
| Phenylbutazone | 1–100 mg |
| Naproxen | 5–100 mg. |

7. The method of claim 6, wherein said NSAID and said carboxylic acid compound are administered at least 2 hours prior to niacin being administered to, released in or absorbed by said patient.

8. The method of claim 7, wherein said NSAID and said carboxylic acid compound are administered from 2 hours to 7 days prior to niacin being administered to, released in or absorbed by said patient.

9. The method of claim 8, wherein said NSAID and said carboxylic acid compound are administered from 2 to 24 hours prior to niacin being administered to, released in or absorbed by said patient.

10. The method of claim 6, wherein said NSAID is aspirin and wherein said aspirin is administered in an amount of from 10 to 40 mg from 2 to 4 times daily.

11. The method of claim 6, wherein said NSAID is in a sustained release formulation.

12. The method of claim 11, wherein said NSAID is aspirin in a sustained release formulation providing an amount of from 3 mg to 100 mg of aspirin per hour to said patient.

13. The method of claim 6, wherein said carboxylic acid compound is citric acid.

14. A method of treating hyperlipimia, comprising
administering to a patient in need thereof niacin as an antilipemic drug, a nonsteroidal anti-inflammatory drug (NSAID) and a carboxylic acid compound other than said NSAID or niacin,
wherein said NSAID and said carboxylic acid compound are administered in an amount effective to reduce cutaneous erythema which niacin causes in said patient,
wherein niacin is administered in an amount effective to treat said hyperlipemia, and
wherein said NSAID is a member selected from the group consisting of aspirin, ibuprofen, indomethacin, phenylbutazone, and naproxen, and
wherein said NSAID is administered in an amount within the following range for that member

| Aspirin | 10–160 mg |
| Ibuprofen | 5–160 mg |
| Indomethacin | 2–10 mg |
| Phenylbutazone | 1–100 mg |
| Naproxen | 5–100 mg. |

15. The method of claim 14, wherein niacin is administered in a manner resulting in niacin being released in or absorbed by said patient at least 2 hours after said NSAID and said carboxylic acid compound are administered.

16. The method of claim 14, wherein said NSAID is aspirin and wherein said aspirin is administered in an amount of from 10 to 40 mg from 2 to 4 times daily.

17. The method of claim 14, wherein said NSAID is in a sustained release formulation.

18. The method of claim 17, wherein said NSAID is aspirin in a sustained release formulation providing an amount of from 3 mg to 100 mg of aspirin per hour to said patient.

19. The method of claim 14, wherein said carboxylic acid compound is citric acid, administered in an amount of from 50 to 500 mg.

20. A composition for treating hyperlipemia, comprising:
an effective amount of niacin to treat said hyperlipemia,
a nonsteroidal anti-inflammatory drug (NSAID), and
a carboxylic acid compound other than said NSAID or niacin,
wherein said NSAID and said carboxylic acid compound are present in a combined amount effective to reduce cutaneous erythma caused by said effective amount of niacin, and
wherein said NSAID is a member selected from the group consisting of aspirin, ibuprofen, indomethacin, phenylbutazone, and naproxen, and
wherein said NSAID is present in an amount up to the amount shown below for that member:

| Aspirin | 160 mg |
| Ibuprofen | 160 mg |
| Indomethacin | 10 mg |
| Phenylbutazone | 100 mg |
| Naproxen | 100 mg. |

21. The composition of claim 20, wherein said carboxylic acid compound is citric acid.

22. The composition of claim 20, wherein said NSAID is aspirin and said composition provides a sustained release of said aspirin in an amount of from 3 mg to 100 mg per hour to said patient.

23. The composition of claim 20, wherein said niacin is enterically coated.

24. The composition of claim 20, comprising a bilayer tablet having first and second layers, in which said first layer comprises said enterically coated niacin, and said second layer comprises said NSAID and said carboxylic acid compound.

25. A composition for treating hyperlipemia, comprising:
(a) an amount of an enterically coated niacin effective to treat said hyperlipemia, and
(b) an amount of a nonsteroidal anti-inflammatory drug (NSAID) effective to reduce cutaneous erythema caused by niacin,
wherein said NSAID is a member selected from the group consisting of aspirin, ibuprofen, indomethacin, phenylbutazone, and naproxen, and
wherein said NSAID is present in an amount up to the amount shown below for that member:

| Aspirin | 160 mg |
| Ibuprofen | 160 mg |
| Indomethacin | 10 mg |
| Phenylbutazone | 100 mg |
| Naproxen | 100 mg. |

26. A method of suppressing cutaneous erythema in a patient to whom niacin is administered, comprising administering to said patient an amount of a sustained release nonsteroidal anti-inflammatory drug (NSAID), effective to reduce said cutaneous erythema caused by niacin, from 4 to 12 hours prior to niacin being administered to, released in, or absorbed by said patient,
wherein said NSAID is a member selected from the group consisting of aspirin, ibuprofen, indomethacin, phenylbutazone, and naproxen, and
wherein said sustained release NSAID provides to said patient an amount per hour within the following range for that member

| Aspirin | 10–160 mg |
| Ibuprofen | 5–160 mg |
| Indomethacin | 2–10 mg |
| Phenylbutazone | 1–100 mg |
| Naproxen | 5–100 mg. |

27. A method of suppressing cutaneous erythema in a patient to whom niacin is administered, comprising administering to said patient an amount of a sustained release aspirin effective to reduce said cutaneous erythema caused by niacin and in an amount providing from 3 mg to 100 mg of aspirin per hour to said patient at least 2 hours prior to niacin being administered to, released in, or absorbed by said patient.

28. A method of treating hyperlipemia, comprising
(a) administering to a patient in need of niacin as an antilipemic drug an amount of a sustained release aspirin effective to reduce cutaneous erythema which niacin causes in said patient and in an amount of from 3 mg to 100 mg of aspirin per hour to said patient, and
(b) administering to said patient an effective amount of niacin to treat said hyperlipemia, wherein niacin is administered in a manner resulting in niacin being released in or absorbed by said patient at least two hours after said aspirin is administered.

* * * * *

UNITED STATES PATENT AND TRADEMARK OFFICE
CERTIFICATE OF CORRECTION

PATENT NO.    : 5,981,555
DATED         : November 9, 1999
INVENTOR(S)   : Kuhrts et al.

It is certified that error appears in the above-identified patent and that said Letters Patent is hereby corrected as shown below:

Column 1,
Line 12, insert -- This invention was made with government support under grant number GM15431 awarded by the National Institute of Health. The government has certain rights in the invention. --

Signed and Sealed this

Eleventh Day of March, 2003

JAMES E. ROGAN
*Director of the United States Patent and Trademark Office*